(12) United States Patent
Sato

(10) Patent No.: US 8,609,417 B2
(45) Date of Patent: Dec. 17, 2013

(54) METHODS AND COMPOSITIONS FOR STEM CELL CULTURES

(75) Inventor: Noboru Sato, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 39 days.

(21) Appl. No.: 13/202,324

(22) PCT Filed: Apr. 13, 2010

(86) PCT No.: PCT/US2010/030899
§ 371 (c)(1),
(2), (4) Date: Aug. 18, 2011

(87) PCT Pub. No.: WO2010/120785
PCT Pub. Date: Oct. 21, 2010

(65) Prior Publication Data
US 2012/0058561 A1    Mar. 8, 2012

Related U.S. Application Data

(60) Provisional application No. 61/168,679, filed on Apr. 13, 2009.

(51) Int. Cl.
| | |
|---|---|
| C12N 1/38 | (2006.01) |
| C12N 5/02 | (2006.01) |
| C12N 9/99 | (2006.01) |
| C12N 15/07 | (2006.01) |

(52) U.S. Cl.
USPC .......... 435/405; 435/383; 435/69.2; 435/70.3

(58) Field of Classification Search
USPC ................. 435/405, 383, 69.2, 70.3
See application file for complete search history.

(56) References Cited

U.S. PATENT DOCUMENTS

2008/0241919 A1 * 10/2008 Parsons et al. ............... 435/366

OTHER PUBLICATIONS

Mader CC et al. Probing Cell Shape Regulation with Patterned Substratum: Requirement of Myosin II-Mediated Contractility, Soft Matter 3: 357-363, 2007.*
Sigma (DME) downloaded from (http://www.sigmaaldrich.com/life-science/cell-culture/learning-center/media-formulations/dme.html) on Jan. 29, 2013, 4 pages.*
Harb N et al. The Rho-Rock-Myosin Signaling Axis Determines Cell-Cell Integrity of Self-Renewing Pluripotent Stem Cells, PloS One, 3 (8): e3001, 2008.*
Engler et al., "Matrxi elasticity irects stem cell lineage specification," Cell, 2006, pp. 677-689, vol. 126.
Harb et al., "The Rho-Rock-Myosin signaling axis determines cell-cell integrity of self-renewing pluripotent stem cells," PlOS One, Aug. 2008, pp. 1-13, vol. 3, No. 8.
Hyojin, Lee, International Search Report and Written Opinion, PCT/2010/030899, Korean Intellectual Property Office, Jan. 28, 2011.
Kim et al., "Substrate rigidity regulates Ca2+ oscillation via RhoA pathway in stem cells," J. of Cellular Phys., Oct. 2008, pp. 285-293, vol. 218.
Ruiz, et al., "Emergence of patterned stem ceell differentiation within multicellular structures," Stem Cells, 2008, pp. 2921-2927, vol. 26.
Shu et al., "Blebbistatin and Blebbistatin-inactivated myosin II inhibit myosin II-independent processes in *Dictyostelium*," PNAS, 2005, pp. 1472-1477, vol. 102, No. 5.

* cited by examiner

*Primary Examiner* — Jon P Weber
*Assistant Examiner* — Larry Moore
(74) *Attorney, Agent, or Firm* — Joseph R. Baker, Jr.; Gavrilovich, Dodd & Lindsey LLP

(57) ABSTRACT

The disclosure provides methods and compositions useful for culturing stem cell including embryonic stem cells, adult stem cells, and embryonic germ cells.

24 Claims, 13 Drawing Sheets

METHODS AND COMPOSITIONS FOR STEM CELL CULTURES

CROSS REFERENCE TO RELATED APPLICATION

This application is a U.S. National Stage Application filed under 35 U.S.C. §371 and claims priority to International Application No. PCT/US10/30899, filed Apr. 13, 2010, which application claims priority to U.S. provisional patent application Ser. No. 61/168,679, filed Apr. 13, 2009, which are each hereby incorporated by reference in their entirety.

TECHNICAL FIELD

The disclosure relates to cell culture technology. Specifically, the disclosure concerns media and culture conditions that can be used for the long-term cultivation of stems cells in a substantially undifferentiated state while maintaining high viability.

BACKGROUND

Stems cells are a potential source from which organs may be regenerated, tissues may be repaired, biological factors prepared or delivered and disease or disorders treated.

SUMMARY

Human pluripotent stem (hPS) cells such as human embryonic stem (hES) and induced pluripotent stem (hiPS) cells are extremely vulnerable under single cell conditions which hamper practical applications. The disclosure demonstrates that treatment with a highly potent inhibitor of nonmuscle myosin II (NMII) (e.g., blebbistatin) substantially enhances survival of hES and hiPS cells under clonal density and suspension conditions, and, in combination with a synthetic matrix, supports a fully defined environment for self-renewal.

This disclosure provides a substantially pathogen-free culture environment for propagation of human induced pluripotent stem (hiPS) cells and human embryonic stem (hES) cells by eliminating animal or human-derived extracellular matrices (ECMs) from the culture procedures. The disclosure demonstrates that inhibition of myosin II increases cell-matrix adhesions and cell survival that efficiently supports self-renewal of hiPS and hES cells on poly-D-lysine coating, a chemically synthesized culture substrate, in a fully defined culture medium. Because the derivation of human pluripotent stem cells utilizes the same culture environment as that for the cell maintenance and expansion, this culture method can also be applied for the derivation of new hiPS and hES cell lines completely free from xeno-derived materials essential for cell-based therapeutic approaches.

Current feeder-free hESCs culture protocols require specific coatings such as Matrigel™, serum components, and human cell-derived ECMs on which hESCs need to adhere to proliferate. The disclosure provides culture compositions and conditions that facilitate stem cell growth in the absence of such coatings and feeder layers. The disclosure impacts hESC culture techniques for at least the following reasons: First, as Matrigel™ or human cell-derived ECM is a mixture of various extracellular matrices such as laminin, fibronectin, and collagen type IV whose composition could be varied from batch to batch, by eliminating the use of cell-derived materials, it is possible to further standardize the hESCs propagation process which is currently highly variable depending on the quality and condition of coating materials; Second, as cell-derived biological materials are never completely free from biological contaminations including viruses and antigens, no requirement of cell-derived coatings would result in a substantial benefit to the development of GMP grade hESCs; Third, although human recombinant ECMs can be produced to circumvent the potential contamination problems, they would not be as competitive as the simple use of plastic tissue culture plates in terms of preparation time, effort and cost; and Fourth, synthetic small molecules are considered to be advantageous for their translation to the clinical settings due to their relatively simple and stable structures. In fact, for example, the Rock inhibitor, Y27632, has been successfully used in clinical studies. Additional chemical inhibitors useful in the methods and compositions of the disclosure are described herein.

The disclosure provides a composition comprising a basal medium and a myosin II inhibitor. The myosin II inhibitor can be blebbistatin or analogue thereof. The basal medium can comprise a fully defined medium. In some embodiments a ROCK inhibitor may also be included in the composition. In certain embodiments, serum including allogeneic or autologous serum to a cell type to be cultured may be included in the composition. In yet another embodiment, the composition may further include amino acids, such as non-essential amino acids. In another embodiment a reducing agent may be included in the composition (e.g., beta mercaptoethanol). Antimicrobial agents and/or antifungal agents may be included in the composition.

The disclosure also provides a composition comprising a basal medium supplemented with non-essential amino acids, an anti-oxidant, a reducing agent, growth factors, a pyruvate salt and a myosin II inhibitor. The myosin II inhibitor can be blebbistatin or an analogue thereof.

The disclosure also provides a kit comprising a poly-D-lysine or a tissue culture plate, flask or growth substrate coated with poly-D-lysine, a defined medium and a myosin II inhibitor. It will be recognized that the kit can be compartmentalized so that a composition of the disclosure can be mixed prior to use. The myosin II inhibitor can be blebbistatin or an analogue thereof.

The disclosure also provides a method of culturing stem cells (including hiPS and ESC), comprising suspending the stem cells in a culture medium comprising a myosin II inhibitor; and culturing the stem cells in the presence of a poly-D-lysine coated tissue culture substrate. In one embodiment, the culture medium is a defined medium. In another embodiment, the culture medium is animal-product free.

The disclosure also provides a stem cell culture, comprising stem cells in a composition comprising a defined medium and a myosin II inhibitor, wherein the stem cells and Neu5Gc free and wherein the stem cells have not been cultured with any animal-product materials (e.g., for at least 1, 2, 5, 10, 20, 30, 40 or 50 or more passages). In one embodiment, the stem cells are cultured in the presence of poly-D-lysine. In one embodiment, the myosin II inhibitor is blebbistatin or an analogue thereof.

Figure 1:
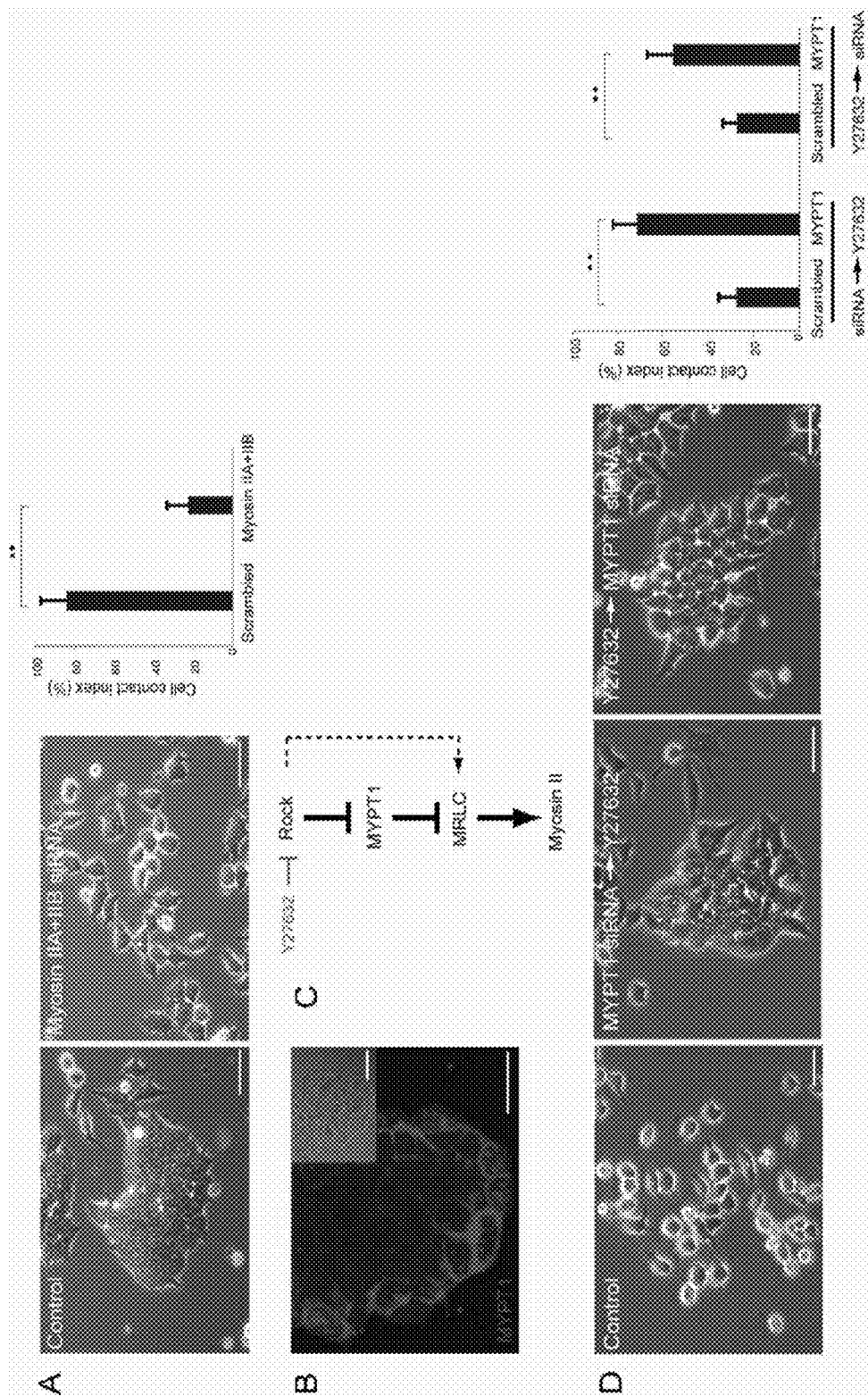
FIG. 1A-D shows myosin II is the canonical effector downstream of Rock in the regulation of cell-cell contact of ES cells (A) Morphology of mES (CJ7) cells transfected with scrambled siRNA showing no effect on cell-cell adhesion whereas cells transfected with siRNA targeting both myosin IIA and IIB exhibited marked disruption of cell-cell contact. The cell contact index supports the morphological observations. Data are mean±SD, p<0.001, n=5. (B) Immunofluorescent analysis locates MYPT1 protein at cell-cell junction sites of undifferentiated ES cells. Inset shows the phase contrast image of the same colony. (C) A scheme depicting the molecular pathway by which Rock regulates myosin II function through the inhibition of MYPT1. The dotted line denotes the alternative Rock function that directly phosphorylates and activates MRLC. (D) In the protection experiment by siRNA, mES cells were transfected with MYPT1 siRNA, and 24 hrs later, they were treated with Y27632 for 24 hrs. The cells were able to maintain their cell-cell integrity against the strong cell-contact disruption effect of the inhibitor. In the rescue experiment, mES cells treated with Y27632 for 24 hrs were subsequently transfected with siRNA targeting MYPT1. Twenty-four hours later, cells were photographed. A substantial proportion of cells were able to restore their cell-cell contacts and formed pre-colony-like structures. The cell-cell contact states were quantified by CCI which represents the morphological observations. Data are mean±SD, p<0.005, n=5. Scale bars, 25 μm.

As those in the art will appreciate, the data and information represented in the attached figures is representative only and do not depict the full scope of the disclosure.

DETAILED DESCRIPTION

As used herein and in the appended claims, the singular forms "a," "and," and "the" include plural referents unless the context clearly dictates otherwise. Thus, for example, reference to "a cell" includes a plurality of such cells and reference to "the agent" includes reference to one or more agents known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Although methods and materials similar or equivalent to those described herein can be used in the practice of the disclosed methods and compositions, the exemplary methods, devices and materials are described herein.

Unless defined otherwise, all technical and scientific terms used herein have the same meaning as commonly understood to one of ordinary skill in the art to which this disclosure belongs. Thus, as used throughout the instant application, the following terms shall have the following meanings.

Pluripotent stem cells are a type of cells that undergo self-renewal while maintaining an ability to give rise to all three germ layer-derived tissues and germ cell lineages. Although pluripotent human embryonic stem (hES) cells derived from human blastocysts are promising sources for cell-based therapies to treat diseases and disorders such as Parkinson's disease, cardiac infarction, spinal cord injury, and diabetes mellitus, their clinical potentials has been hampered by their immunogenicity and ethical concerns.

The disclosure demonstrates that the Rho-Rock-Myosin II (RRM) signaling axis regulates cell-cell and cell-matrix interactions, and cell survival of both hiPS and hES cells.

Based on this information the disclosure provides a culture system combining a chemical inhibitor of myosin II (e.g., a chemical inhibitor selective for myosin II). Furthermore, the disclosure demonstrates that hES and hiPS growth on defined synthetic D-lysine can be used to grow hES and hiPS cells. Accordingly, the further addition of myosin II inhibitors (e.g., such as blebbistatin and analogs thereof) at a low concentration in combination with a single synthetic matrix, and completely defined medium provides a culture system that reduced (or eliminates) the presence of pathogens from human derived or animal derived culture systems.

Cell types that can be cultured using the media of the disclosure include stem cells derived from any mammalian species including humans, monkeys, and apes and include embryonic stem cells, embryonic germ cells, and Nanog iPS cells (see, e.g., Nature, 448:313-318, July 2007; and Takahashi et al., Cell, 131(5):861-872; which are incorporated herein by reference). For example, induced pluripotent stem cells (iPSs, or iPSCs) are a type of pluripotent stem cell obtained from non-pluripotent cells by selective gene expression (of endogenous genes) or by transfection with a heterologous gene.

Induced pluripotent stem cells are described by Shinya Yamanaka's team at Kyoto University, Japan. Yamanaka had identified genes that are particularly active in embryonic stem cells, and used retroviruses to transfect mouse fibroblasts with a selection of those genes. Eventually, four key pluripotency genes essential for the production of pluripotent stem cells were isolated; Oct-3/4, SOX2, c-Myc, and Klf4. Cells were isolated by antibiotic selection for Fbx15$^+$ cells. The same group published a study along with two other independent research groups from Harvard, MIT, and the University of California, Los Angeles, showing successful reprogramming of mouse fibroblasts into iPS and even producing a viable chimera.

While iPS cells are virtually identical to ES cells at molecular and functional levels, there are critical hurdles to translation of their therapeutic potentials into medical applications. One of the issues is that because the current standard protocols for reprogramming and propagation of iPS cells include animal-derived materials that are unsuitable for potential clinical purposes, a fully defined method to generate and expand hiPS cells needs to be developed.

The culture environment for hiPS and hES cells basically relies on the two major elements, namely, culture medium and ECM coatings, the latter of which include Matrigel, a cocktail of mouse tumor cell-derived ECMs broadly used for the feeder-free culture method. Although recent progresses in understanding the self-renewal mechanisms have led to manufacturing fully defined culture medium, due to the complexity of the structural components of ECMs and insufficient accumulation of basic studies focusing on cell-cell or cell-matrix interactions of pluripotent stem cells, the development of coating methods that meet the rigorous clinical standards still remains as a major challenge.

Cell migration, myosin synthesis, and ECM interactions are important in the development of cells, their differentiation as well as the development of certain diseases such as atherosclerosis, arthritis, and glomerular nephritis. The initial event in cell migration is polarization and extension of protrusions in the direction of migration. Rho family small GTPases control the formation of these protrusions (lamellipodia and filopodia) by regulating the cytoskeleton and cell adhesion. Rac and Cdc42 are involved in the formation of lamellipodia and filopodia, respectively, and Rho is involved in stress fiber formation and contraction. Coordinated regulation by these Rho family members enables cells to migrate.

Upon stimulation of cells by agonists, the GDP-bound form of Rho family small GTPases are converted to the GTP-bound form, and they interact with their effector molecules. Rho regulates myosin phosphorylation through its effector molecules, such as Rho-kinase/ROCK/ROK and the myosin binding subunit (MBS) of myosin phosphatase (Kimura et al. 1996). Activated Rho interacts with Rho-kinase and MBS and activates Rho-kinase. Subsequently, the activated Rho-kinase phosphorylates the myosin light chain (MLC) and MBS. Phosphorylation of MBS inactivates myosin phosphatase.

ESCs are derived from the inner cell mass (ICM) of a blastocyst. ESCs can grow infinitely (self-renewal) while maintaining the ability to generate all somatic cell types and germ cell lineages (pluripotency). This specific stem cell function has been investigated at the molecular level, leading to the identification of the key roles of master transcription factors such as Oct3/4 and Nanog, and secreted signaling molecules including leukemia inhibitory factor (LIF), bone morphogenetic proteins (BMP) and Wnt. Recent derivation of hESCs has opened the door to the use of pluripotent stem cells as a source of the cell transplantation therapy for the treatment of diseases such as Parkinson's disease and diabetes mellitus. With exponentially increasing demand for hESCs research toward medical applications, it is essential to investigate how to regulate pluripotency in order to develop uncompromised technologies to derive and expand hESCs that is at the stem of entire cell therapeutic strategies before inducing any differentiated type of adult cells.

Stem cells are cells capable of differentiation into other cell types, including those having a particular, specialized function (e.g., tissue specific cells, parenchymal cells and progenitors thereof). Progenitor cells (i.e., "multipotent") are cells that can give rise to different terminally differentiated cell types, and cells that are capable of giving rise to various progenitor cells. Cells that give rise to some or many, but not all, of the cell types of an organism are often termed "pluripotent" stem cells, which are able to differentiate into any cell type in the body of a mature organism, although without reprogramming they are unable to de-differentiate into the cells from which they were derived. As will be appreciated, "multipotent" stem/progenitor cells (e.g., neural stem cells)

have a more narrow differentiation potential than do pluripotent stem cells. Another class of cells even more primitive (i.e., uncommitted to a particular differentiation fate) than pluripotent stem cells are the so-called "totipotent" stem cells (e.g., fertilized oocytes, cells of embryos at the two and four cell stages of development), which have the ability to differentiate into any type of cell of the particular species. For example, a single totipotent stem cell could give rise to a complete animal, as well as to any of the myriad of cell types found in the particular species (e.g., humans).

As can be appreciated, there is great interest in isolating and growing stem cells for use in transplantation, cell regeneration and replacement therapy, drug discovery, generation of model systems for studying mammalian development, and gene therapy. However, current culture conditions are limited in their ability to maintain isolated stem cells in an undifferentiated yet proliferative state. For example, embryonic stem cells and germ cells can be maintained using feeder-free cultures that have been supplemented with leukemia inhibitory factor (LIF). On the other hand, conventional techniques for maintaining human embryonic stem cells lead to their rapid differentiation when the cells are cultured without an appropriate feeder cell layer or conditioned medium from a suitable feeder cell line, even in the presence of LIF.

Additionally, current methods of culturing undifferentiated stem cells require such things as the use of serum in addition to a feeder cell layer (or conditioned medium from an appropriate feeder cell line). The requirement for components such as serum, feeder cells, and/or conditioned medium complicates the process of cultivating stem cells and additionally, for in vivo use, the culture conditions can result in contamination by xenogenic materials. Moreover, the use of feeder cells and xenogenic culture components (e.g., fetal calf serum and the like) increases the risk that the stem cells may be contaminated with unwanted components (e.g., aberrant cells, viruses, cells that may induce an immune response in a recipient of the stem cell population, heterogeneous fusion cells, and the like), thus limiting the therapeutic potential of stem cells as therapeutics or in the production of therapeutics.

The disclosure provides compositions, methods and systems for the culturing of stem cell in the absence of animal products. Accordingly, the disclosure provides animal product-free stem cells, methods of using such stem cells and compositions comprising such stem cells. The disclosure also provides methods and compositions for culturing stem cell in a fully defined medium, in the absence of feeder cells and animal material while maintaining high viability (e.g., equal to or higher than typical stem cell culture techniques) and maintaining the cells in an undifferentiated state. The disclosure comprises methods and compositions that modify cell signaling during stem cell maintenance, thereby preventing differentiation yet maintaining robust cell proliferation. For example, a culture of the disclosure will lack N-glycolylneuraminic acid (Neu5Gc) and/or Lactate Dehydrogenase-elevating Virus (LDEV) that are contaminants resulting from cultures in the presence of animal products.

The disclosure demonstrates that myosin II inhibition by a selective chemical inhibitor, blebbistatin, enhances cell-matrix interactions and cell survival of hiPS and hES cells, a key element to successfully growth of human pluripotent stem cells under clinically relevant culture environments.

Furthermore, because the culture condition for the derivation process of hiPS cells and hES cells are essentially the same as that for regular maintenance and growth of human pluripotent stem cells, the technology developed in this disclosure can be applied for generating new hiPS and hES cell lines that are free from animal-derived materials.

Cell-cell contact is achieved by synergistic collaboration of various adhesion molecules, their interconnected scaffold proteins, and actin-cytoskeletons that are regulated by specific intracellular signaling pathways. Although studies have revealed that several extracellularly secreted signaling molecules such as LIF, BMP, FGF, TGF-β/Nodal, and Wnt are important for the pluripotent genetic programs, very little is known about the functional significance of the specific intracellular signaling molecules that control the cell-cell communication and integration in pluripotent ESCs.

Cell-cell contact is regulated by various types of adhesion molecules and interconnected cytoskeletal machineries including myosin, ATP-driven molecular motors, which also determines cell architectures and polarized cell functions. siRNA-mediated loss of function experiments demonstrated a requirement of non-muscle myosin II for cell adhesion in ES cells. Myosin II, the two-headed conventional myosin, consists of three isoforms, IIA, IIB, and IIC, of which all, except IIC, are expressed in ES cells whereas differentiated cells express all three isoforms. Strikingly when myosin IIA and IIB isoforms were simultaneously depleted, cells showed disintegration of the cell-cell contact phenocopying that was seen in cells with loss of function of Rho or Rock. Rock phosphorylates and inactivates MYPT1 to protect the phosphorylated, active form of MRLC that drives myosin II function. MYPT1 was found to be exclusively localized to cell-cell contact sites in mES cells. If Rock controls the myosin function through inhibition of MYPT1 in mES cells, depletion of MYPT1 would rescue the intrinsic cell-cell communications from the robust effect of the Rock inhibitor. Consistent with this hypothesis, depletion of MYPT1 before or after the inhibitor treatment resulted in significant protection or restoration of cell-cell contact, respectively.

ESCs retain high nuclear/cytoplasmic ratio with small cell size, and undergo tight colony formation when they are grown in the undifferentiated state. They however exhibit larger and flattened morphology when they start differentiation, and occasionally decrease cell-cell contact followed by migration to the outside of the colony. Despite the descriptive nature of the morphological observations, as it accurately represents the specific biological state of stem cells, the morphology is still routinely used as a primary and reliable readout to determine the differentiation status of ESCs.

Signaling to the cytoskeleton through, for example, G protein coupled receptors (GPCRs), integrins and receptor tyrosine kinases (RTKs) can lead to diverse effects on a cell's activity, including changes in cell shape, migration, proliferation and survival. Integrins, in conjunction with other components of focal adhesion (FA) complexes, serve as the link between the extracellular matrix and the cytoskeleton. Integrin activation leads to activation of focal adhesion kinase (FAK) and Src kinase, resulting in the phosphorylation of other FA components such as paxillin and the Crk-associated substrate p130 CAS, as well as the recruitment of signaling adaptor proteins. This is accompanied by actin assembly, in addition to changes in FA dynamics and FA turnover.

In a similar fashion, RTKs utilize intrinsic tyrosine kinase activity to phosphorylate sites on their intracellular loops and/or on associated signaling components. This leads to the recruitment of adaptor proteins and signaling kinases that modulate downstream mediators of phosphoinositide signaling, small GTPase activation, and MAP kinase cascades. GPCR utilize heterotrimeric G protein-initiated second messengers to couple to similar signaling mechanisms impacting on actin dynamic behavior.

Intracellular regulation of the cell's response to external cues occurs through a large number of signaling cascades that include the Rho family of small GTPases (Rho, Rac and cdc42) and their activators, guanine nucleotide exchange factors (GEFs), as well as downstream protein kinase effectors, including Rho-kinase/ROCK and p21 activated kinase (PAK). These cascades converge on proteins that regulate the behavior of the actin cytoskeleton, including actin interacting regulatory proteins such as cofilin, Arp2/3, Ena/VASP, formins, profilin and gelsolin. Signaling through different pathways can lead to the formation of distinct actin-dependent structures whose coordinated assembly/disassembly is important for directed cell migration and other cellular behaviors. Migration is also regulated by signaling to myosin, which participates in leading edge actin dynamics and enables retraction of the rear of the cell.

Rho is a small GTP-binding protein that has been suggested to be the central integrator of myelin-derived growth inhibitory signals (McKerracher and Winton, Neuron, 36:345-348, 2002). In the absence of myelin-associated inhibitors (such as MAG or Nogo-A), nerve growth and regeneration are believed to occur as a result of Rho-GDI-induced suppression of Rho activity. In one non-limiting mechanism, myelin-associated inhibitors (such as MAG and Nogo-A) bind to NgR, which, in turn, binds to and activates p75. Activated p75 sequesters Rho-GDI away from Rho, allowing Rho to become activated through the exchange of GDP for GTP. The activated GTP-bound Rho then interacts with signaling proteins such as Rho kinase (ROCK) to suppress axonal growth and regeneration (reviewed in Kaplan and Miller, Nat. Neurosci., 6:435-436, 2003).

Rho GTPase family proteins, which include RhoA, Rac1 and Cdc42, control a wide variety of cellular processes such as cell morphology, motility, proliferation, differentiation and apoptosis (Hall, 1994; Van Aelst and D'Souza-Schorey, 1997).

The Rho-associated coiled-coil forming protein serine/threonine kinase (ROCK) family members are effectors of Ras-related small GTPase Rho. The ROCK family includes p160ROCK (ROCK-1), ROKα/Rho-kinase/ROCK-II, protein kinase PKN, and citron and citron kinase. ROCK has been implicated in various diseases and disorders including hypertension, cerebral vasospasm, coronary vasospasm, bronchial asthma, erectile dysfunction, glaucoma, vascular smooth muscle cell proliferation, myocardial hypertrophy, malignoma, ischemia/reperfusion-induced injury, endothelial dysfunction, Crohn's Disease and colitis, neurite outgrowth, Raynaud's Disease, angina, Alzheimer's disease, atherosclerosis, and cardiac hypertrophy and perivascular fibrosis.

The two isoforms of ROCK include ROCK1 (which may also be referred to as ROK-β or p160ROCK) and ROCKII (which may also be referred to as ROK-α or Rho-kinase). The two isoforms have 65% sequence similarity overall, and the kinase domains comprise 92% sequence identity. Although both isoforms are ubiquitously expressed in tissues, there are differing intensities in certain tissues.

ROCK1 is a RhoA-binding protein with Ser/Thr protein kinase activity and is 1358 amino acids in length. The polypeptide includes a catalytic kinase domain at the N-terminus, which is about 300 amino acids in length and comprises the conserved motifs characteristic of Ser/Thr kinases; the kinase domain is also involved in binding to RhoE, which is a negative regulator of ROCK activity. In addition, the C-terminus of ROCK1 has several functional domains, including a Rho-binding domain within a flexible coiled-coil region, a pleckstrin homology (PH) domain, and a cysteine-rich domain. In some embodiments, the PH domain is likely necessary for regulation by interacting with lipid messengers, for example, arachidonic acid. Autoinhibitory activity of ROCK is demonstrated upon interaction of the carboxyl terminus with the kinase domain to reduce kinase activity. The Rho-binding domain, which is about 80 amino acids in length and is required for interaction with activated RhoA, comprises considerable sequence similarity to domains present in some Rho binding proteins.

Exemplary ROCK inhibitors include Y-27632 and fasudil, which bind to the kinase domain to inhibit its enzymatic activity in an ATP-competitive mechanism. Negative regulators of ROCK activation include small GTP-binding proteins such as Gem, RhoE, and Rad, which can attenuate ROCK activity. H-1152 dihydrochloride (H-1152P-2HCl; (S)-(+)-2-Methyl-1-[(4-methyl-5-isoquinolinyl)sulfonyl]homopiperazine) can also be used. Additional ROCK inhibitors include those described in International Application Publication Nos.: WO 01/56988; WO 02/100833; WO 03/059913; WO 02/076976; WO 04/029045; WO 03/064397; WO 04/039796; WO 05/003101; WO 02/085909; WO 03/082808; WO 03/080610; WO 04/112719; WO 03/062225; and WO 03/062227, for example. In some of these cases, motifs in the inhibitors include an indazole core; a 2-aminopyridine/pyrimidine core; a 9-deazaguanine derivative; benzamide-comprising; aminofurazan-comprising; and/or a combination thereof. For example, WO 03/080610 relates to imidazopyridine derivatives as kinase inhibitors, such as ROCK inhibitors, and methods for inhibiting the effects of ROCK1 and/or ROCK2. The disclosures of the applications cited above are incorporated herein by reference.

Another inhibitor of Rho is S-farnesylthiosalicylic acid (FTS) and its derivatives and analogs. Another inhibitor is imidazole-containing benzodiazepines and analogs (see, e.g., WO 97/30992). The Rho inhibitor can also act downstream by interaction with ROCK (Rho activated kinase) leading to an inhibition of Rho. Such inhibitors are described in U.S. Pat. No. 6,642,263 (the disclosures of which are incorporated by reference herein in their entirety). Other Rho inhibitors that may be used are described in U.S. Pat. Nos. 6,642,263, and 6,451,825. Such inhibitors can be identified using conventional cell screening assays, e.g., described in U.S. Pat. No. 6,620,591 (all of which are herein incorporated by reference in their entirety). In specific embodiments of the disclosure, ROCK1 is targeted instead of ROCK 2, wherein the agent binds to an allosteric site resulting in inhibition of ROCK1.

As only the active form of Rho GTPase can signal to the downstream pathways by binding to the specific effector proteins (Rho kinase and mammalian homologue of Diaphanous, mDia, for the Rho signaling pathway), they are considered to be the molecular switch that spatiotemporally integrates actin cytoskeletons and molecular motors into the specific conformation of the higher subcellular structures (FIG. 1). Although the critical roles of the Rho family proteins for various aspects of biological function have been extensively studied in a number of different cell types, the investigation of their role for stem cell regulation is described here.

Studies have indicated that Rho GTPases play key roles for controlling stem cell functions in adult skin, hematopoietic, and mesenchymal stem cells. The disclosure demonstrates that ESCs utilize the Rho signaling pathway to control cell-cell integrity while maintaining pluripotency.

Figure 5:
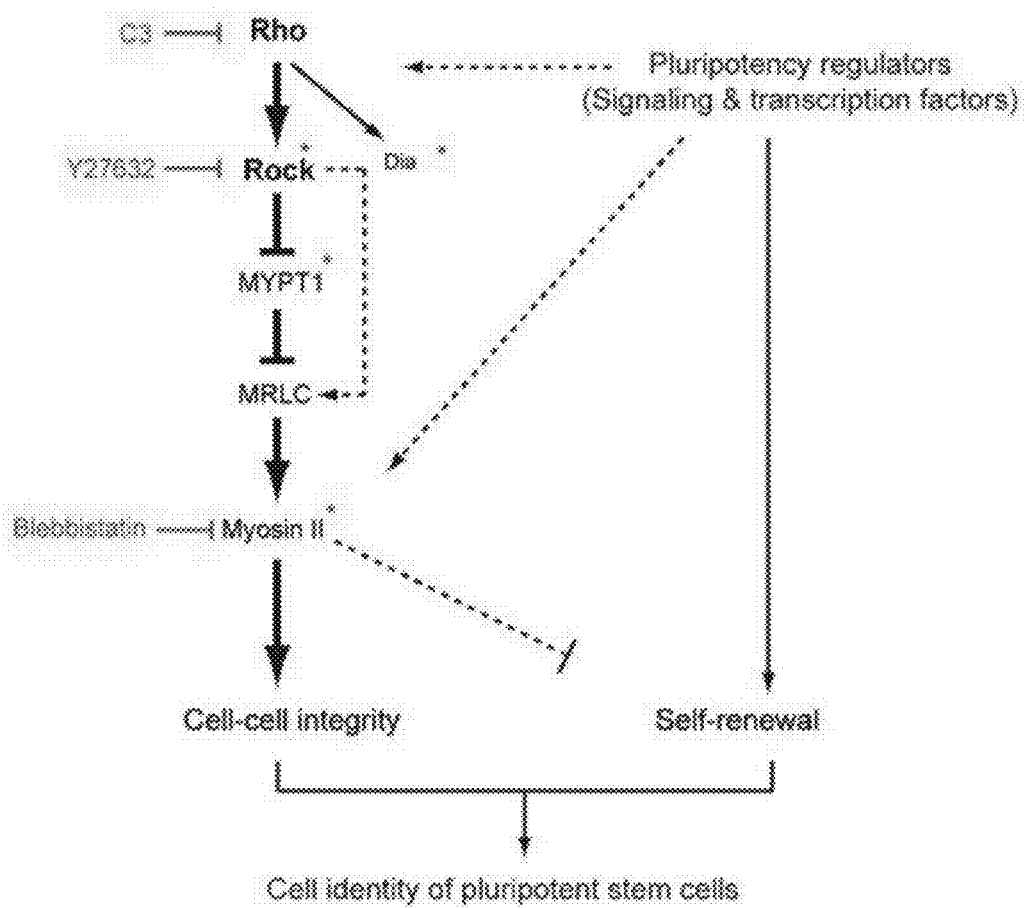
FIG. 5 shows a model summarizing the Rho-Rock-Myosin signaling pathway that regulates basic cell-cell interactions in ES cells. Chemicals and siRNAs used in the study are highlighted in red and asterisks, respectively. Dotted lines indicate potential mechanistic interactions within or between the cell-integrity and self-renewal pathways. Arrows denote activation and bars indicate inhibition.

The disclosure demonstrates that inhibition of ROCK results in the ability of stem cells (e.g., human embryonic stem cells—hESCs and induced stem cells) to grow on plastic dishes without requirement of any coatings such as extracellular matrices. Furthermore, the disclosure demonstrates that inhibition of myosin II activity also modulates the ability of stem cells (e.g., hES and hiPS) to grow and maintain pluripotency (see, e.g., FIG. 5 for a schematic of the described pathway).

In one embodiment, a culture media comprising a myosin II inhibitor is provided. In another embodiment, a culture media comprising a ROCK inhibitor, a myosin II inhibitor or a combination thereof is provided. The culture media is useful for culturing stem cells including hESC and hiPS cells in the absence of a feeder layer or extracellular matrix coated tissue culture material. In another embodiment, the culture media is used to culture stem cells on a poly-D-lysine coated tissue culture material.

In yet another embodiment, the culture media can comprise other components in addition to a ROCK inhibitor, a myosin II inhibitor or combination of thereof. For example, the culture media can comprise amino acids (e.g., non-essential amino acids), antibiotics, fungicides, growth factors, LIF, sulfur containing biological active compounds (e.g., beta-mercaptoethanol), pyruvate (e.g., sodium pyruvate), serum (e.g., human serum, bovine serum) and any combinations thereof. Preferably any additional agents will be derived from the same species as the stem cells to be cultured or be chemically synthesized. In yet a further preferred embodiment, the cell culture media and the culture conditions lack any animal derived products.

the disclosure is based, in part, on the discovery of biological agents that can be used to promote the proliferation and robustness of stem cells in culture in the absence of animal derived products. In addition, the disclosure is based on the discovery that the biological agents of the disclosure also promote the growth, replication and robustness of stem cell cultures in the absence of a feeder layer. The media can be essentially serum-free, and does not require the use of a feeder cell layer or conditioned medium from separate cultures of feeder cells, although in some embodiments it can be used to initially culture the stem cells in a growth environment that includes allogeneic feeder cells (or conditioned medium from such cells) prior to transferring the cells to fresh, feeder-free cultures for serial passaging (e.g., 1-50 or more passages).

A medium according to the disclosure comprises a myosin II inhibitor, ROCK inhibitor or a combination thereof. The medium may also include, without limitation, non-essential amino acids, an anti-oxidant, a reducing agent, growth factors, and a pyruvate salt. The base media may, for example be Dulbecco's Modified Eagle Medium (DMEM), DMEM/F-12, or KO-DMEM, each supplemented with L-glutamine (e.g., including the dipeptide L-alanyl-L-glutamine (Invitrogen)), non-essential amino acids, and β-mercaptoethanol. A medium is typically sterilized (e.g., by filtration) prior to addition to a cell culture. The medium may also be supplemented with antibiotics and fungicides.

Exemplary myosin II inhibitors include blebbistatin (Synonyms: 1-Phenyl-1,2,3,4-tetrahydro-4-hydroxypyrrolo[2,3-b]-7-methylquinolin-4-one; $C_{18}H_{16}N_2O_2$) and analogues having the general formula I:

Formula I

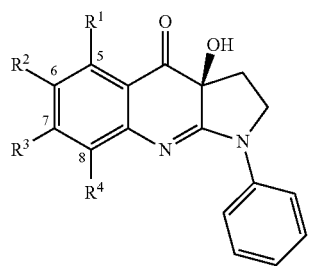

wherein $R^{1-4}$ are each individually a methyl or hydrogen.

Blebbistatin blocks branching, elongation. However, less specific myosin inhibitors may be used, such as BDM. There are several functional analogues of Blebbistatin published in a literature (Lucas-Lopez et al. 2008). Because myosin II function is regulated by myosin light chain kinase (MLCK), MLCK inhibitors such as ML-7 and ML-9 can be also used to block the activity of myosin II. In one embodiment, a blebbistatin concentration of between about 1.25-10 μM for is useful. Among this range, the compound has been routinely used for long term cell culture at 2.5 μM in combination with poly-D-lysine coating which exhibits substantially high and consistent plating efficiency and anti-apoptotic effects on human ES and iPS cells.

A growth factor refers to a substance that is effective to promote the growth of stem cells and which, unless added to the culture medium as a supplement, is not otherwise a component of the basal medium. Growth factors include, but are not limited to, basic fibroblast growth factor (bFGF), acidic fibroblast growth factor (aFGF), epidermal growth factor (EGF), insulin-like growth factor-I (IGF-I), insulin-like growth factor-II (IGF-II), platelet-derived growth factor-AB (PDGF), and vascular endothelial cell growth factor (VEGF), activin-A, Wnt and bone morphogenic proteins (BMPs), insulin, cytokines, chemokines, morphogents, neutralizing antibodies, other proteins, and small molecules.

Exogenous growth factors may also be added to a medium according to the disclosure to assist in the maintenance of cultures of stem cells in a substantially undifferentiated state. Such factors and their effective concentrations can be identified as described elsewhere herein or using techniques known to those of skill in the art of culturing cells. Representative examples of growth factors useful in the compositions and methods of the disclosure include bFGF, insulin, acidic FGF (aFGF), epidermal growth factor (EGF), insulin-like growth factor I (IGF-I), IGF-II, platelet-derived growth factor (PDGF), and vascular endothelial growth factor (VEGF), activin-A, bone morphogenic proteins (BMPs), forskolin, glucocorticords (e.g., dexamethasone), transferrins, and albumins.

Basal medium refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cell's survival. These are compounds that the cells themselves can not synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of basal media are known in the art of mammalian cell culture, such as Dulbecco's Modified Eagle Media (DMEM), Knockout-DMEM (KO-DMEM), and DMEM/F12, although any base medium that can be supplemented with bFGF, insulin, and ascorbic acid and which supports the growth of stem cells in a substantially undifferentiated state can be employed.

"Conditioned medium" refers to a growth medium that is further supplemented with soluble factors derived from cells cultured in the medium. Techniques for isolating conditioned medium from a cell culture are well known in the art. As will be appreciated, conditioned medium is preferably essentially cell-free. In this context, "essentially cell-free" refers to a conditioned medium that contains fewer than about 10%, preferably fewer than about 5%, 1%, 0.1%, 0.01%, 0.001%, and 0.0001% than the number of cells per unit volume, as compared to the culture from which it was separated.

A "defined" medium refers to a biochemically defined formulation comprised solely of the biochemically-defined constituents. A defined medium may include solely constituents having known chemical compositions. A defined medium may also include constituents that are derived from known sources. For example, a defined medium may also include factors and other compositions secreted from known tissues or cells; however, the defined medium will not include the conditioned medium from a culture of such cells. Thus, a "defined medium" may, if indicated, include a particular compound added to form the culture medium, up to and including a portion of a conditioned medium that has been fractionated to remove at least one component detectable in a sample of the conditioned medium that has not been fractionated. Here, to "substantially remove" one or more detectable components of a conditioned medium refers to the removal of at least an amount of the detectable, known component(s) from the conditioned medium so as to result in a fractionated conditioned medium that differs from an unfractionated conditioned medium in its ability to support the long-term substantially undifferentiated culture of primate stem cells. Fractionation of a conditioned medium can be performed by any method (or combination of methods) suitable to remove the detectable component(s), for example, gel filtration chromatography, affinity chromatography, immune precipitation, and the like. Similarly, or a "defined medium" may include serum components derived from an animal, including human serum components. In this context, "known" refers to the knowledge of one of ordinary skill in the art with reference to the chemical composition or constituent.

A cell culture is "essentially feeder-free" when it does not contain exogenously added conditioned medium taken from a culture of feeder cells nor exogenously added feeder cells in the culture, where "no exogenously added feeder cells" means that cells to develop a feeder cell layer have not been purposely introduced for that reason. Of course, if the cells to be cultured are derived from a seed culture that contained feeder cells, the incidental co-isolation and subsequent introduction into another culture of some small proportion of those feeder cells along with the desired cells (e.g., undifferentiated stem cells) should not be deemed as an intentional introduction of feeder cells. Similarly, feeder cells or feeder-like cells that develop from stem cells seeded into the culture shall not be deemed to have been purposely introduced into the culture.

A "non-essential amino acid" refers to an amino acid species that need not be added to a culture medium for a given cell type, typically because the cell synthesizes, or is capable of synthesizing, the particular amino acid species. While differing from species to species, non-essential amino acids are known to include L-alanine, L-asparagine, L-aspartic acid, L-glutamic acid, glycine, L-proline, and L-serine.

A cell culture is "essentially serum-free" when it does not contain exogenously added serum. If the cells being cultured produce some or all of the components of serum, or if the cells to be cultured are derived from a seed culture grown in a medium that contained serum, the incidental co-isolation and subsequent introduction into another culture of some small amount of serum (e.g., less than about 1%) should not be deemed as an intentional introduction of serum.

Useful reducing agents include beta-mercaptoethanol. Other reducing agents such as monothioglycerol or dithiothreitol (DTT), alone or in combination, can be used to similar effect. Still other equivalent substances will be familiar to those of skill in the cell culturing arts.

Pyruvate salts may also be included in a medium according to the disclosure. Pyruvate salts include sodium pyruvate or another pyruvate salt effective maintaining and/or enhancing stem cell growth in a substantially undifferentiated state such as, for example, potassium pyruvate.

Other compounds suitable for supplementing a culture medium of the disclosure include nucleosides (e.g., adenosine, cytidine, guanosine, uridine, and thymidine) and nucleotides. Nucleosides and/or nucleotides can be included in a variety of concentrations.

As will be appreciated, it is desirable to replace spent culture medium with fresh culture medium either continually, or at periodic intervals, typically every 1 to 3 days. One advantage of using fresh medium is the ability to adjust conditions so that the cells expand more uniformly and rapidly than they do when cultured on feeder cells according to conventional techniques, or in conditioned medium.

Populations of stem cells can be obtained that are 4-, 10-, 20-, 50-, 100-, 1000-, or more fold expanded when compared to the previous starting cell population. Under suitable conditions, cells in the expanded population will be 50%, 70%, or more in the undifferentiated state, as compared to the stem cells used to initiate the culture. The degree of expansion per passage can be calculated by dividing the approximate number of cells harvested at the end of the culture by the approximate number of cells originally seeded into the culture. Where geometry of the growth environment is limiting or for other reasons, the cells may optionally be passaged into a similar growth environment for further expansion. The total expansion is the product of all the expansions in each of the passages. Of course, it is not necessary to retain all the expanded cells on each passage. For example, if the cells expand two-fold in each culture, but only about 50% of the cells are retained on each passage, then approximately the same number of cells will be carried forward. But after four cultures, the cells are said to have undergone an expansion of 16-fold. Cells may be stored by cryogenic freezing techniques known in the art.

Embryonic stem cells are generated and maintained using methods well known to the skilled artisan such as those described by Doetschman et al. (1985) J. Embryol. Exp. Mol. Biol. 87:27-45). Any line of ES cells can be used. One mouse strain that is typically used for production of ES cells, is the 129J strain. Another ES cell line is murine cell line D3 (American Type Culture Collection, catalog no. CKL 1934). Still another ES cell line is the WW6 cell line (Ioffe et al. (1995) PNAS 92:7357-7361). Human embryonic stem cells (hESCs) can be isolated, for example, from human blastocysts obtained from human in vivo preimplantation embryos, in vitro fertilized embryos, or one-cell human embryos expanded to the blastocyst stage (Bongso, et al. (1989), Hum. Reprod., vol. 4: 706). Human embryos can be cultured to the blastocyst stage in G1.2 and G2.2 medium (Gardner, et al. (1998), Fertil. Steril., vol. 69:84). The zona pellucida is removed from blastocysts by brief exposure to pronase (Sigma). The inner cell masses can be isolated by immunosurgery or by mechanical separation, and are plated on mouse embryonic feeder layers, or in the defined culture system as described herein. After nine to fifteen days, inner cell mass-derived outgrowths are dissociated into clumps either by exposure to calcium and magnesium-free phosphate-buffered saline (PBS) with 1 mM EDTA, by exposure to dispase, collagenase, or trypsin, or by mechanical dissociation with a micropipette. The dissociated cells are then replated as before in fresh medium and observed for colony formation. Colonies demonstrating undifferentiated morphology are individually selected by micropipette, mechanically dissociated into clumps, and replated. Embryonic stem cell-like morphology is characterized as compact colonies with apparently high nucleus to cytoplasm ratio and prominent nucleoli. Resulting embryonic stem cells are then routinely split every 1-2 weeks by brief trypsinization, exposure to Dulbecco's PBS (without calcium or magnesium and with 2 mM EDTA), exposure to type IV collagenase (about 200 U/mL), or by selection of individual colonies by mechanical dissociation, for example, using a micropipette.

Once isolated, the stem cells can be cultured in a culture medium according to the disclosure that supports the substantially undifferentiated growth of stem cells using any suitable cell culturing technique. For example, a matrix laid down prior to lysis of primate feeder cells (preferably allogeneic feeder cells) or a synthetic or purified matrix can be prepared using standard methods. The stem cells to be cultured are then added atop the matrix along with the culture medium. In other embodiments, once isolated, undifferentiated stem cells can be directly added to an extracellular matrix that contains laminin or a growth-arrested human feeder cell layer (e.g., a human foreskin fibroblast cell layer) and maintained in a serum-free growth environment according to the culture methods of disclosure. In yet another embodiment, the stem cells can be directly added to a biocompatible cell culture plate in the absence of an extracellular matrix material (e.g., directly on polystrene, glass or the like). Unlike existing embryonic stem cell lines cultured using conventional techniques, embryonic stem cells and their derivatives prepared and cultured in accordance with the methods of the disclosure avoid or have reduced exposure to xenogeneic antigens that may be present in feeder layers. This is due in part to the media compositions promoting growth in the absence of feeder layers or directly on a cell culture substrate. This avoids the risks of contaminating human cells, for example, with non-human animal cells, transmitting pathogens from non-human animal cells to human cells, forming heterogeneous fusion cells, and exposing human cells to toxic xenogeneic factors.

The cell culture media of the disclosure and methods for growing stem cells in accordance with the disclosure will be seen to be applicable to all technologies for which stem cell lines are useful. For example, cells cultured based upon the media and methods of the disclosure can be used for screening to identify growth factors useful in culturing stem cells in an undifferentiated state, as well as compounds that induce such cells to differentiate toward a particular cell or tissue lineage. The disclosure also allows genetically modified stem cells to be developed, as well as the creation of new stem cell lines.

The disclosure also provides kits comprising a myosin II inhibitor and various basal media compositions. In some embodiments, the kits may further include one or more ROCK inhibitors, a cell culture substrate. In some embodiments, the can comprise a substantially purified poly-D-lysine for coating on a substrate or the cell culture substrate may be pre-coated with a poly-D-lysine. The kits can be compartmentalized to maintain separation of the biological agent until use at which point it can be added to the basal media.

Culture conditions of the disclosure comprise a culture medium according to the disclosure and a cell culture vessel that typically includes a biocompatible substrate that supports the undifferentiated growth of stem cells. In one embodiment, the biocompatible substrate is a solid, such as a plastic, ceramic, metal, or other biocompatible material to which cells can adhere. In one embodiment, the biocompatible substrate comprises a poly-lysine (e.g., a poly-D-lysine). The biocompatible substrate can exclude any extracellular matrix compositions. However, in some aspects, it may be useful to provide a minimal amount of matrix material. Typically the matrix material is derived from the same species as the cell type. For example, a composition (e.g., a matrix) to which cells can adhere can be used. In one embodiment, the matrix can be, but is not limited to, nylon (polyamides), dacron (polyesters), polystyrene, polypropylene, polyacrylates, polyvinyl compounds (e.g., polyvinylchloride), polycarbonate (PVC), polytetrafluorethylene (PTFE; TEFLON), thermanox (TPX), nitrocellulose, cotton, polyglycolic acid (PGA), cat gut sutures, cellulose, gelatin, dextran, collagen, fibronectin and various combinations thereof. Where the matrix material or coating on culture vessel includes biological material that can be found in a living organism, preferably, the matrix material is chemically synthesized to avoid the presence of any animal products or cell culture material that may contaminate a culture environment.

A culture vessel can be any shape and size including a well in multi-well tissue culture plate, or as large as a stirred tank bioreactor. For large-scale applications, the surface area for cell attachment can be increased by the use of microbeads or other substrates that can be suspended in a culture medium (e.g., plastic beads or polymers) or the like may be used, either coated or uncoated.

Using such methods, populations of stem cells, e.g., human embryonic stem cells or hiPS cells, can be isolated from the resulting cell cultures, thereby representing another embodiment of the disclosure. Such populations can be isolated by any suitable technique. Such techniques include affinity chromatography, panning, and fluorescence-assisted cell sorting. Such techniques each employ one or more separation reagents (for example, but not restricted to, antibodies and antibody fragments, reporter genes/proteins and the like) that are specific for a cell-based marker indicative of an undifferentiated state. In the context of substantially undifferentiated human embryonic stem cells, such markers include, for example, but not restricted to the transcriptional factors Oct-4 and Nanog, and cell surface markers SSEA-4, Tra-1-60, and Tra-1-81. Other markers include telomerase, Myc, p300, and Tip60 histone acetyltransferases, acetylated histones, and alkaline phosphatase. Negative selection can also be employed, whereby cells that express one or more markers indicative of other than a substantially undifferentiated state, or alternatively, cells which fail to express a particular marker, can be removed from the desired cell population. Such populations can be used to produce stable stem cell lines, including cell lines of stem cells such as human embryonic stem cells. If desired, such cells can be genetically modified to, for example, alter (i.e., increase or decrease) the expression of one or more endogenous genes, and/or express one or more genes introduced into the cells. Such genetic modifications can serve, for example, to correct genetic defects detected in a particular stem cell line, as well as to generate abnormal cell lines (which may be useful as model systems that mimic or replicate a genetic context correlated with a particular disease state). An isolated population of such stem cells of the disclosure can be defined as being animal-material free stem cells (i.e., they have not been cultured in combination with any animal obtain material).

Yet other embodiments of the disclosure relate to methods of using stem cells, including substantially undifferentiated stem cells, cultured or isolated in accordance with the disclosure. For instance, such cells can be used to identify factors that promote the cell's differentiation, or, alternatively, their continued maintenance in a substantially undifferentiated state or de-differentiation to a more primitive state (e.g., going from a multipotent stem cell to a pluripotent or totipotent stem cell). Briefly, in the context of differentiation or maintenance of a substantially undifferentiated state, such methods involve, for example, exposing a myosin II inhibitor, ROCK inhibitor or combination thereof to substantially undifferentiated stem cells that are being cultured in a culture medium of the disclosure. Following exposure to the test compound, the cells are assessed to determine if they have been better maintained in a substantially undifferentiated state or induced to differentiate by the biological agent(s). If the cells have been better maintained in a substantially undifferentiated state, the biological agent can be identified as one that promotes an undifferentiated state or self-renewal of stem cells. If the cells have been induced to differentiate, the test compound can be identified as one that promotes differentiation of substantially undifferentiated stem cells. The differentiating cells may be followed to determine their developmental fate, in other words, to determine what cell lineage they become as a result of differentiating. In the context of de-differentiation, cells of a more differentiated state (e.g., hematopoietic stem cells) are exposed to one or more compounds and then assessed to determine if the exposure resulted in cells of a more primitive type (e.g., a stem cell) than those initially exposed to the test compound. If so, the compound that produces the effect is identified as one that promotes de-differentiation, or reprogramming, of cells. Typically, these and other screening methods according to the disclosure are conducted in a high throughput manner, such that numerous compounds can be simultaneously screened.

Another embodiment of the disclosure comprises isolation, establishment, and culturing of stem cell lines, particularly undifferentiated human embryonic stem cell lines, in a non-animal based, defined growth environment according to the disclosure. For example, stem cells cultured in accordance with the disclosure, particularly pluripotent undifferentiated human embryonic stem cells (hESCs) or hiPS cells and their derivatives (e.g., hESC-derived multipotent neural stem cells, hematopoietic precursor cells, cardiomyocytes, and insulin-producing cells and the like) that are cultivated and maintained in a xeno-free growth environment, can be used therapeutically. Representative therapeutic uses include cell-based therapies to treat disorders such as heart diseases, diabetes, liver diseases, neurodegenerative diseases, cancers, tumors, strokes, spinal cord injury or diseases, Alzheimer's diseases, Parkinson's diseases, multiple sclerosis, amyotrophic lateral sclerosis (ALS), and disorders caused by single gene defects. In such methods, a patient in need of such therapy is administered a population of substantially undifferentiated human embryonic stem cells or differentiated cells derived from substantially undifferentiated human embryonic stem cells. The cells so administered may be genetically modified, although this is not essential.

Another embodiment of the disclosure concerns methods of directing the fate of stem cells, in terms of differentiation toward a specific tissue or cell lineage. In examples of such methods, substantially undifferentiated stem cells (e.g., human embryonic stem cells), for instance, are induced to differentiate into a particular cell type or lineage by administering one or more factors that promote such differentiation. Conversely, the disclosure also concerns methods for re-programming more developmentally committed cells to become more primitive or immature. For instance, human hematopoietic stem cells are induced to de-differentiate into cells that can give rise to cell types not only of the hematopoietic lineage but also other, non-hematopoietic cell types. In one embodiment, the cells are cultured in a media comprising a myosin II inhibitor, a ROCK inhibitor or both on a poly-D-lysine substrate to grow and maintain undifferentiated pluripotent cell type. The undifferentiated cells are then differentiated by replacing or adding to the culture medium a differentiation medium or factor.

The following Examples are provided to illustrate certain aspects of the disclosure and to aid those of skill in the art in practicing the disclosure. These Examples are in no way to be considered to limit the scope of the disclosure in any manner.

EXAMPLES

Chemicals. Blebbistatin (InSolution™ Blebbistatin), Y-27632 (InSolution™ Y-27632), and ML-7 were purchased from EMD. PDL was obtained from Millipore.

Cell culture. Two independent hES cell lines, H9 (WiCell) and BGN01 (BresaGen), were examined. hiPS cells used in the study include iPS (Foreskin) Clone 1 (WiCell) and two independently derived hiPS cells from normal human dermal fibroblasts (NHDF) which have been characterized by a series of molecular and functional assays. For the regular feeder-free culture, hES or hiPS cells were grown on Matrigel (BD Biosciences)-coated plates in a defined medium, mTeSR (StemCell Technologies). Cells were regularly passaged by the standard method using dispase (Invitrogen) or trypsin-EDTA (Lonza). General stem cell culture techniques are described in Freshney et al., Culture of Human Stem Cells (Culture of Specialized Cells), John Wiley & Sons, 1992 (the disclosure of which is incorporated herein by reference for all purposes). mES cells used in the experiment include CJ7, E14, RW4 (a parental line of NMHCIIA$^-$/A$^-$ mES cells), NMHCIIA$^-$/A$^-$, and NMHCIIB$^-$/B$^-$ mES cells. Cells were maintained on either mitotically inactivated mouse embryonic fibroblasts or gelatin (Sigma)-coated dishes with the standard medium in the presence of leukemia inhibitory factor (LIF) at 1400 U/ml (Millipore). For the microscopic or immunofluorescent analysis, cells were plated at approximately 5000-10000 cells/cm$^2$. For the defined culture, cells were plated at approximately 10000 cells/cm$^2$ on plates freshly coated with PDL or PDL-precoated plates (BD Bioscience) in mTeSR supplemented with 2.5 to 5 µM of blebbistatin or Y-27632. Medium was changed every day or every other day depending on confluency. Cells were passaged by using trypsin-EDTA every 3 to 4 days.

For the cell growth assay, hiPS or hES cells were plated at $2.5 \times 10^4$ cells/cm$^2$ on plates coated with PDL or Matrigel in mTeSR in the presence of blebbistatin at 5 µM or Y-27632 at 5 µM (PDL) or in the absence of compounds (Matrigel). Cells were harvested at the indicated time points, stained with trypan blue, and counted by the hemocytometer.

Clonal Assay.

hES or hiPS cells in mTeSR supplemented with or without blebbistatin were plated on Matrigel-coated 96-well plates at a single cell per well. Seven days after plating, cells were subjected to alkaline phosphatase assay using Alkaline Phosphatase Detection Kit (Millipore) according to the manufacturer's instruction.

Cell Viability Assay.

hES or hiPS cells were plated at $1 \times 10^5$ cells/well on 12-well plates coated with PDL or Matrigel in mTeSR in the presence or absence of blebbistatin or Y-27632 at various concentrations in triplicates. DMSO (solvent for blebbistatin) was also added in the control condition and found to have no effect on viability. For mES cells, cells were plated under the same condition except for the use of gelatin coating and mES medium. After 24 h, cells were harvested, trypsinized to single cells, and counted by hemocytometer. Cell counting was performed independently by two researchers to confirm the consistency. The same samples were used for TUNEL assay immediately after taking a small fraction of the sample for cell counting.

For the evaluation of cell viability under suspension culture, hES or hiPS cells were plated at $5 \times 10^5$ in non-tissue culture-treated 6-well plates with non-conditioned standard hESm containing blebbistatin or Y-27632 at different concentrations in triplicates. After 2 days, cells were harvested with trypsinization and extensive trituration by pipetting, and the number of live cells was manually counted by using hemocytometer and trypan blue staining. The cell survival ratio (%) represents the ratio of the number of live cells to the number of cells plated. The same samples were subjected to TUNEL assay for side by side comparison with the data from cell viability assay.

Immunostaining.

For immunocytochemistry, cells grown on culture vessels were fixed in 4% paraformaldehyde (USB Corporation). After washing with PBS/BSA, the samples were incubated with primary antibodies recognizing the target proteins at 4° C. overnight. The primary antibodies used in the study include Oct3 (BD Biosciences), myosin IIA (Covance), and myosin IIB (Covance). The samples were washed for three times, and incubated with appropriate secondary antibodies conjugated with Alexa Fluorophore (Invitrogen) at room temperature for 30 min. After three times washing, the samples were counterstained with 4',6-diamidino-2-phenylindole (DAPI, Invitrogen), and examined by Nikon TE-2000-U fluorescent inverted microscope (Nikon Instruments) equipped with CFI Fluor 40× objective or Zeiss LSM 510 confocal microscopy equipped with Apochromate water-immersion lenses (Carl Zeiss).

For immunohistochemistry, paraffin sections of teratoma samples were immersed in xylene and a series of graded ethanol followed by incubation with primary antibodies against nestin, α-fetoprotein, or α-smooth muscle actin (all from Chemicon) at 4° C. overnight. The rest of the processes including the incubation with the secondary antibodies were the same as those described above.

TUNEL Assay.

The samples in triplicates used for cell viability assay were immediately tested by TUNEL assay by using APO-DIRECT kit (BD Pharmingen) according to the manufacturer's protocol. The number of TUNEL (FITC) or propidium iodide (PI)-positive cells was counted by hemocytometer under fluorescent microscopy with 20× objective. When necessary, FITC-labeled cells were verified by using 40× objective to exclude non-specific signal. At least 300 cells were evaluated per each sample and counting was repeated for 2 times. The ratio of the number of TUNEL-positive cells to the number of PI-positive cells was calculated. The representative result was shown in the figure from experiments repeated for at least 3 times. Although flow cytometric analysis was initially attempted, due to persistent cell aggregations from suspension culture experiments even after extensive trypsinization and trituration, we decided to switch to manual cell counting which well correlated with the data obtained from cell viability assay.

QPCR. Total RNA was isolated from cells by using Qiashredder and RNAeasy mini kit (Qiagen). The extracted RNA sample was quantified by UV spectrophotometer, and qualified by the RNA Nano Lab chip (Agilent Technologies). Two µg of total RNA was reverse-transcribed using SuperScript III RT-PCR system (Invitrogen) according to the manufacturer's protocol. Each cDNA sample in triplicates was PCR amplified with specific PCR primers and FullVelocity SYBR Green QPCR master mix (Stratagene) using MyiQ real-time PCR detection system (BioRad). Each cycle threshold (CT) value was determined by iQ5 optical system software (BioRad), and normalized by the β-actin expression level. The primer sequences were designed by Primer Express software (Applied Biosystems), and their potential crossreactivity with other sequences were prescreened by In Silico PCR (University of California, Santa Cruz). All sequences used for primers are shown in the table below.

Teratoma Formation.

All animal-related protocols were approved by Institutional Animal Care and Use Committee. Cells (approximately $2 \times 10^6$ cells) grown under defined conditions for multiple passages with occasional freezing and thawing were subcutaneously injected into severe combined immunodeficient (SCID)/beige mice (Charles River Laboratories). After 4 to 8 weeks, the developed teratomas were excised, fixed in 4% paraformaldehyde or 10% formalin, and subjected to histological section preparations.

Western Analysis.

Total protein was extracted with RIPA buffer (20 mM Tris-HCl, pH 7.5, 150 mM NaCl, 1 mM $Na_2$EDTA, 1 mM EGTA, 1% NP-40, 1% sodium deoxycholate, 2.5 mM sodium pyrophosphate, 1 mM β-glycerophosphate, 1 mM $Na_3VO_4$, and protease inhibitors). Protein concentrations were determined by BCA Protein Assay kit (Pierce). An equal amount (20 µg) of protein was loaded in each lane, separated by 10% SDS/PAGE, and transferred onto a PVDF membrane (Bio-Rad). The membrane was blocked in Odyssey blocking buffer (LI-COR Biotechnology), and subsequently incubated with primary antibodies against Oct3 (Santa Cruz Biotechnology), Nanog (Millipore), myosin IIA (Covance), myosin IIB (Covance), cleaved caspase-3 (Cell Signaling), or β-actin (Sigma) at 4° C. overnight followed by incubation with peroxidase-conjugated goat anti-mouse IgG or goat anti-rabbit IgG (Jackson ImmunoResearch, Inc.), and developed with ECL reagent (GE Healthcare).

Embryoid Body (EB) Formation.

Cells were harvested by using dispase or trypsin-EDTA, plated on non-tissue culture treated dishes (approximately $10^6$ cells/well/6-well plate) in the absence of compounds, and grown in non-conditioned hES medium for 14 days. Cells were harvested for protein extraction, and subjected to Western.

Karyotyping.

Standard G-banded karyotyping was carried out for each cell line approximately every 10 to 20 passages.

Statistical Analysis.

Biological replicates (3 to 5 replicates per condition) were subjected to statistical analysis by using analysis of variance (ANOVA) or paired t-test. The statistical significance was shown as the probability value such as **$p<0.01$. Data points are shown as mean±standard deviation (SD).

Myosin II Regulates Cell-Cell Adhesions Downstream of Rock.

Figure 2:
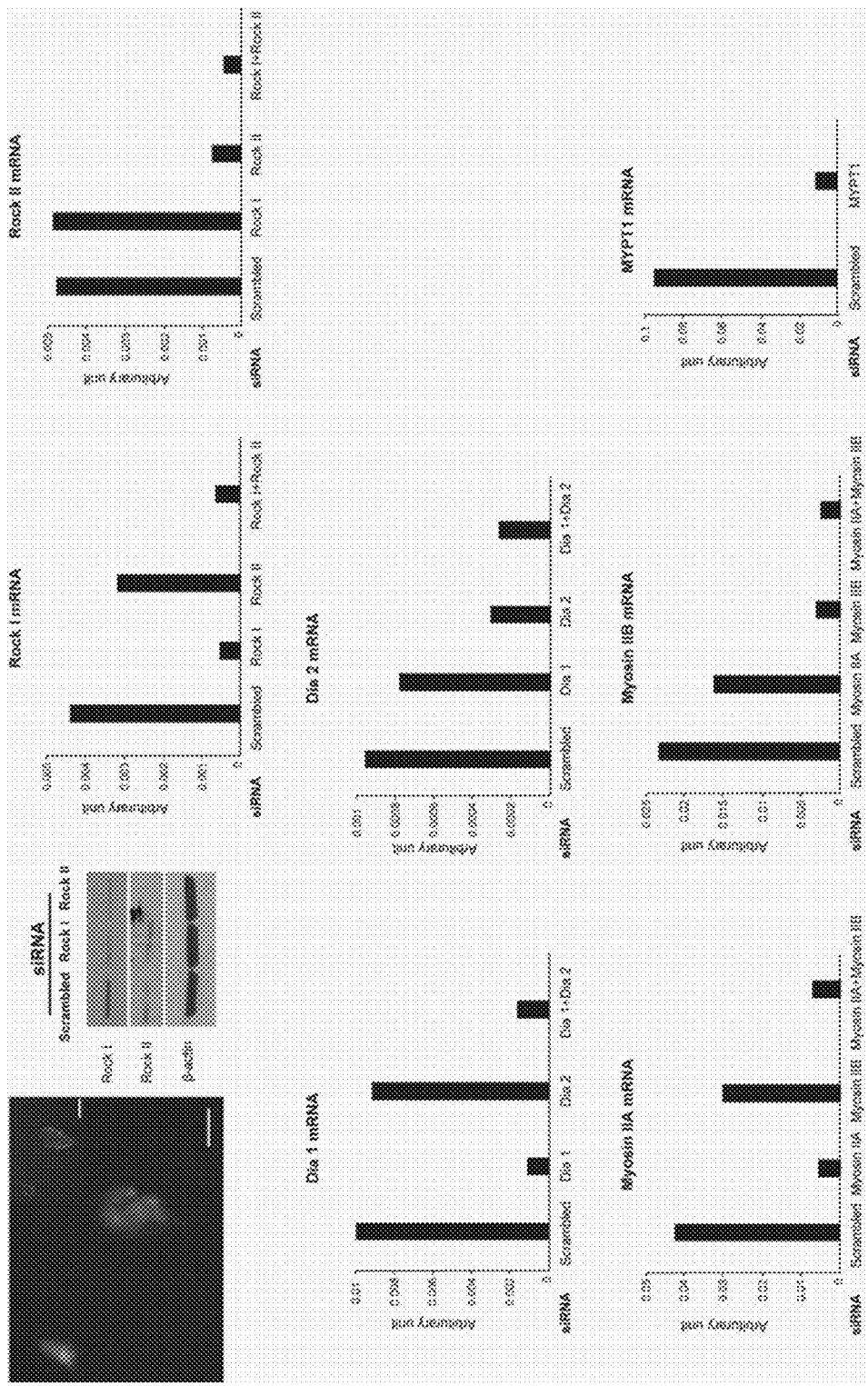
FIG. 2 shows siRNA-mediated gene silencing in ES cells. To determine the transfection efficiency of siRNA in mES cells, cells were transfected with green fluorophore (FAM)-tagged siRNA at 40 nM with use of Lipofectamine 2000, and 24 hrs later, cells were evaluated on fluorescent inverted microscope. Virtually almost all cells incorporated fluorophore-tagged siRNA. Inset denotes the phase contrast image. To evaluate the level of knockdown of endogenous genes by siRNA treatment, mES cells were transfected with each siRNA targeting specific gene at 40 nM or at 25 nM when two distinct siRNAs were combined. 24 hrs later, cells were harvested, and subjected to Western or QPCR analysis. For Western analysis, β-actin was used as a loading control. Although the effect of Rock I siRNA appeared to be isoform-specific, Rock II siRNA affected both isoforms in a similar manner. Hence, the effect of Rock siRNA on the cell-cell contact was evaluated only when both Rock I and Rock II were simultaneously depleted by the cotransfection of Rock I and Rock II siRNAs. For the QPCR analysis, the data were normalized to the expression level of β-actin. The endogenous mRNA level of myosin IIC in mES cells was two orders below that of other myosins. Although myosin IIC-specific siRNA treatment further reduced the expression level down to 40% that of the control, no substantial effects on cell-cell contact was observed. Scale bars, 25 μm.

Rho and Rho-associated kinase (Rock) play a role in regulation of cell-cell interactions in pluripotent stem cells. In order to further explore the core mechanism underlying cell-cell adhesions, principle regulators downstream of Rock were examined. Based on functional prescreening non-muscle myosin II was identified as an effector by siRNA-mediated loss of function analysis. Non-muscle Myosin II (myosin II), the two-headed conventional myosin, consists of non-muscle myosin II heavy chain (NMHC) dimers and two sets of myosin light chains (MLCs). There are three different NMHCs, NMHC IIA, NMHC IIB, and NMHC IIC, encoded by Myh9, Myh10, and Myh14 genes, respectively, each of which exhibits distinct functions in mammals. Among them, all the genes except IIC are expressed in pluripotent stem cells whereas differentiated cells express all three isoforms. When myosin IIA and IIB isoforms were simultaneously depleted, cells exhibited remarkable disintegration of the cell-cell contact phenocopying loss of function of Rho or Rock (FIG. 1A). The specificity and levels of knockdown of the target genes by each siRNA were confirmed by quantitative RT-PCR (QPCR) (FIG. 2). Myosin phosphatase target subunit 1 (MYPT1), a major downstream target of Rock that negatively regulates myosin function through phosphorylation of myosin regulatory light chain (MRLC) was examined. MYPT1 was exclusively localized to cell-cell contact sites in mES cells (FIG. 1B). If Rock controls the myosin function through inhibition of MYPT1, depletion of MYPT1 would rescue the intrinsic cell-cell interactions from the robust effect of Y27632 (FIG. 1C). Supporting this hypothesis, depletion of MYPT1 before or after the inhibitor treatment resulted in significant protection or restoration of cell-cell contact, respectively (FIG. 1D). Existence of a fraction of cells insensitive to the siRNA treatment suggests the alternative regulation of myosin II by Rock-mediated direct activation of MRLC. Collectively, these data suggest that cell-cell contacts in ES cells are regulated by the Rho-Rock-Myosin II (RRM) signaling axis.

siRNA sequences (P - represents a short palindromic domain)

| Target gene | Pool duplex | Primer | Sequence |
|---|---|---|---|
| Rock I | 1 | Sense | GCAAAGAGAUUGUUAGAAU (SEQ ID NO: 1) |
| | 2 | Sense | AGACACAGCUGUAAGAUUA (SEQ ID NO: 2) |
| | 3 | Sense | UGUCGAAGAUGCCAUGUUA (SEQ ID NO: 3) |
| | 4 | Sense | GACCUUCAAGCACGAAUUA (SEQ ID NO: 4) |
| Rock II | 1 | Sense | GAGAUUACCUUACGGAAAAUU (SEQ ID NO: 5) |
| | | Antisense | 5'-(P)UUUUCCGUAAGGUAAUCUCUU (SEQ ID NO: 6) |
| | 2 | Sense | GGACAUGAGUUUAUUCCUAUU (SEQ ID NO: 7) |
| | | Antisense | 5'-(P)UAGGAAUAAACUCAUGUCCUU (SEQ ID NO: 8) |
| | 3 | Sense | GCAAUGAAGCUUCUUAGUAUU (SEQ ID NO: 9) |
| | | Antisense | 5'-(P)UACUAAGAAGCUUCAUUGCUU (SEQ ID NO: 10) |
| | 4 | Sense | CACAACAGAUGAUCAAAUAUU (SEQ ID NO: 11) |
| | | Antisense | 5'-(P)UAUUUGAUCAUCUGUUGUGUU (SEQ ID NO: 12) |
| Dia 1 | 1 | Sense | GUACAGCUGUGCGUGUUUG (SEQ ID NO: 13) |
| | 2 | Sense | GAAGUUGUCUGUAGAGGAA (SEQ ID NO: 14) |
| | 3 | Sense | GGAACAGUAUAACAAACUA (SEQ ID NO: 15) |
| | 4 | Sense | GAAACCAGCAUGAGAUUAU (SEQ ID NO: 16) |
| Dia 2 | 1 | Sense | GAUGACCGAUCUUUGAUUUUU (SEQ ID NO: 17) |
| | | Antisense | 5'-(P)AAAUCAAAGAUCGGUCAUCUU (SEQ ID NO: 18) |
| Myosin IIA | 1 | Sense | GAGCGAGCCUCCAGGAAUAUU (SEQ ID NO: 19) |
| | | Antisense | 5'-(P)UAUUCCUGGAGGCUCGCUCUU (SEQ ID NO: 20) |
| | 2 | Sense | GCACCAAGCUCAAGCAGAUUU (SEQ ID NO: 21) |
| | | Antisense | 5'-(P)AUCUGCUUGAGCUUGGUGCUU (SEQ ID NO: 22) |
| | 3 | Sense | GAACCGAACUGGCCGACAAUU (SEQ ID NO: 23) |
| | | Antisense | 5'-(P)UUGUCGGCCAGUUCGGUUCUU (SEQ ID NO: 24) |
| | 4 | Sense | GAAGGUGGCUGCCUACGAUUU (SEQ ID NO: 25) |
| | | Antisense | 5'-(P)AUCGUAGGCAGCCACCUUCUU (SEQ ID NO: 26) |
| Myosin IIB | 1 | Sense | GGACUUAUCUAUACUUACUUU (SEQ ID NO: 27) |
| | | Antisense | 5'-(P)AGUAAGUAUAGAUAAGUCCUU (SEQ ID NO: 28) |
| | 2 | Sense | GAGCGUACAUUUCAUAUCUUU (SEQ ID NO: 29) |
| | | Antisense | 5'-(P)AGAUAUGAAAUGUACGCUCUU (SEQ ID NO: 30) |
| | 3 | Sense | UGAGGCAGCUAGUAUUAAAUU (SEQ ID NO: 31) |
| | | Antisense | 5'-(P)UUUAAUACUAGCUGCCUCAUU (SEQ ID NO: 32) |
| | 4 | Sense | GUAUUAAGUUUGCGAAGGAUU (SEQ ID NO: 33) |
| | | Antisense | 5'-(P)UCCUUCGCAAACUUAAUACUU (SEQ ID NO: 34) |
| Myosin IIC | 1 | Sense | CUGAAGAAAGACCGCAAUAUU (SEQ ID NO: 35) | siRNA sequences (P - represents a short palindromic domain)

| Target gene | Pool duplex | Primer | Sequence |
|---|---|---|---|
| | | Antisense | 5'-(P)UAUUGCGCUCUUUCU-UCAGUU (SEQ ID NO: 36) |
| | 2 | Sense | UCAAGGACCAUUACCGAAAUU (SEQ ID NO: 37) |
| | | Antisense | 5'-(P)UUUCGGUAAUGGUCCU-UGAUU (SEQ ID NO: 38) |
| | 3 | Sense | ACGCAGAGGUAGAGCGCGAUU (SEQ ID NO: 39) |
| | | Antisense | 5'-(P)UCGCGCUCUACCU-CUGCGUUU (SEQ ID NO: 40) |
| | 4 | Sense | AGGCGGAACUUGAGAGCGUUU (SEQ ID NO: 41) |
| | | Antisense | 5'-(P)ACGCUCUCAAGUUCCGC-CUUU (SEQ ID NO: 42) |
| MYPT1 | 1 | Sense | GAACGAGACUUGCGUAUGUUU (SEQ ID NO: 43) |
| | | Antisense | 5'-(P)ACAUACGCAAGUCUCGUU-CUU (SEQ ID NO: 44) |
| | 2 | Sense | AAGAAUAGUUCGAUCAAUGUU (SEQ ID NO: 45) |
| | | Antisense | 5'-(P)CAUUGAUCGAACUAUUCU-UUU (SEQ ID NO: 46) |
| | 3 | Sense | CGACAUCAAUUACGCCAAUUU (SEQ ID NO: 47) |
| | | Antisense | 5'-(P)AUUGGCGUAA-UUGAUGUCGUU (SEQ ID NO: 48) |
| | 4 | Sense | UCGGCAAGGUGUUGAUAUAUU (SEQ ID NO: 49) |
| | | Antisense | 5'-(P)UAUAUCAACACCUUGC-CGAUU (SEQ ID NO: 50) |

Real-time QPCR primer sequences (SEQ ID NO)

| Gene | | Sequence |
|---|---|---|
| mouse_beta-actin | Forward | 5'-CGAGGCCCAGAGCAAGAG-3' (51) |
| | Reverse | 5'-CGTCCCAGTTGGTAACAATGC-3' (52) |
| mouse_Rock I | Forward | 5'-ATTCATTCCTACCCTCTACCACTTT C-3' (53) |
| | Reverse | 5'-GCTTAAAGACATGCCACAAAGGT-3' (54) |
| mouse_Rock II | Forward | 5'-GCGATGCTGAGCCTGATGAT-3' (55) |
| | Reverse | 5'-GCACAGGCAATGACAACCAT-3' (56) |
| mouse_Dia 1 | Forward | 5'-GGATGCACAGGAACAGTATAACAAA-3' (57) |
| | Reverse | 5'-AAGACGAAGTAGTCACCTAGCTCCT T-3' (58) |
| mouse_Dia 2 | Forward | 5'-CAGTCAGGTGCAGCATTCAGA-3' (59) |
| | Reverse | 5'-GGGTCTTACCTGGATTTCTTGGA-3' (60) |
| mouse_Myosin IIA | Forward | 5'-TGGCAAGCAAGCGTGTGT-3' (61) |
| | Reverse | 5'-GCCGATGCGGTACAGGTT-3' (62) |
| mouse_Myosin IIB | Forward | 5'-TCCTCACGCCCAGGATCA-3' (63) |
| | Reverse | 5'-GCCAATGCTTCCACTGCAA-3' (64) |
| mouse_Myosin IIC | Forward | 5'-GCAATGCCAAGACGGTGAA-3' (65) |
| | Reverse | 5'-GATGTAGCCAGCAATATCAAAGTTG A-3' (66) |
| mouse_MYPT1 | Forward | 5'-GACTCCCCCGGGTTCCT-3' (67) |
| | Reverse | 5'-CCTCAGCCCACAAACGATTT-3' (68) |
| mouse_Pou5f1 | Forward | 5'-TGGCGTGGAGACTTTGCA-3' (69) |
| | Reverse | 5'-GAGGTTCCCTCTGAGTTGCTTTC-3' (70) |
| mouse_Nanog | Forward | 5'-TGTGCACTCAAGGACAGGTTTC-3' (71) |
| | Reverse | 5'-CAGGTTCAGAATGGAGGAGAGTTC-3' (72) |
| mouse_FGF5 | Forward | 5'-CAACACGTCTCCACCCACTTC-3' (73) |
| | Reverse | 5'-TTTCTGGAACAGTGACGGTGAA-3' (74) |
| mouse_Snail1 | Forward | 5'-CCACTGCAACCGTGCTTTT-3' (75) |
| | Reverse | 5'-CACATCCGAGTGGGTTTGG-3' (76) |
| mouse_N-Cadherin | Forward | 5'-GGGTCTGTTCCAGAGGGATCA-3' (77) |
| | Reverse | 5'-GGATCATCCGCATCAATGG-3' (78) |
| human_Oct3 | Forward | 5'-GAAGCCTTTCCCCCTGTCTCT-3' (79) |
| | Reverse | 5'-AAGGGCAGGCACCTCAGTT-3' (80) |
| human_Nanog | Forward | 5'-AATGAAATCTAAGAGGTGGCAGAA A-3' (81) |
| | Reverse | 5'-TTCTGCGTCACACCATTGCT-3' (82) |
| human_FGF5 | Forward | 5'-GCAGCCCCCGGGTTAA-3' (83) |
| | Reverse | 5'-GCTCCGACTGCTTGAATCTTG-3' (84) |
| human_Slug | Forward | 5'-CCATTCCACGCCCAGCTA-3' (85) |
| | Reverse | 5'-TCACTCGCCCCAAAGATGAG-3' (86) |

-continued

| Real-time QPCR primer sequences (SEQ ID NO) | | |
|---|---|---|
| human_GATA6 | Forward | 5'-GGATTGTCCTGTGCCAACTGT-3' (87) |
| | Reverse | 5'-GGTTCACCCTCGGCGTTT-3' (88) |
| Mouse Pou5f1 | Forward | 5'-TGGCGTGGAGACTTTGCA-3' (89) |
| | Reverse | 5'-GAGGTTCCCTCTGAGTTGCTTTC-3' (90) |

Figure 3:
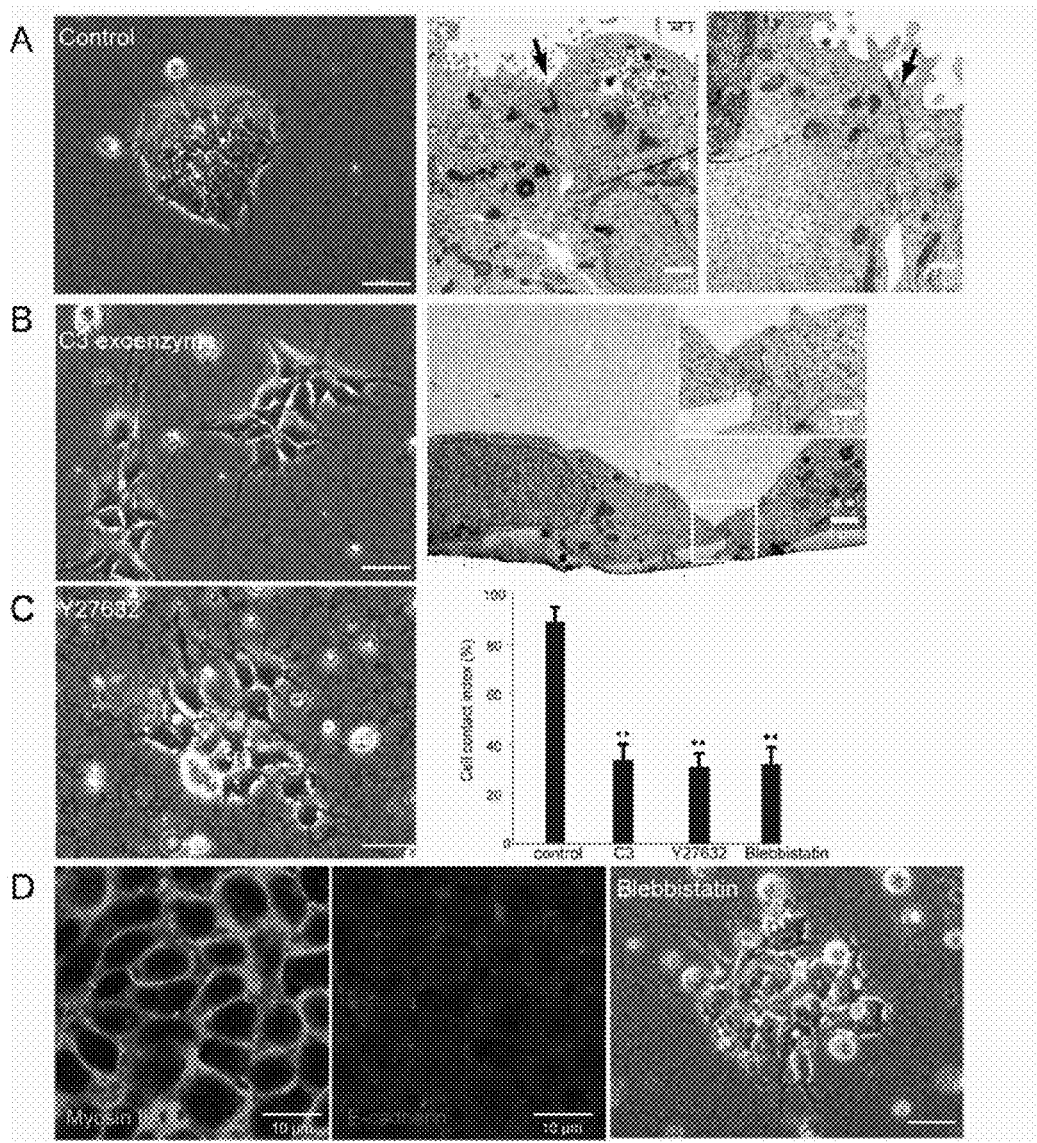
FIG. 3A-D shows the Rho-Rock-Myosin II signaling axis in the regulation of cell-cell communication is conserved in hES cells. (A) Morphology of undifferentiated hES cells (H9) showing a tightly connected colony. Ultrastructural analysis by transmission electron microscopy demonstrates specialized junctional complexes at cell-cell contact sites (arrow). (B) hES cells treated with C3 exoenzyme (20 μg/ml) for 24 hrs exhibited disruption of close cell-cell connections. Ultrastructural analysis shows that C3-treated cells occasionally contact with neighboring cells through small areas at the cell periphery (inset). (C) Y27632 disassembled cell-cell junctions in hES cells grown on Matrigel at a higher (20 μM) concentration than that (10 μM) for mES cells. Cell contact index summarizes the effect of the inhibitors on hES cells. Data are mean±SD, **p<0.001, n=5. (D) Immunofluorescence analysis of hES cells grown under the control condition show the exclusive localization of myosin IIA at cell-cell contact sites that overlaps with E-cadherin subcellular distribution. A myosin II-specific synthetic inhibitor, Blebbistatin (10 μM), disrupted cell-cell connections in hES cells similar to that seen in C3 or Y27632-treated cells. Scale bars, 25 μm.

Rock and myosin II regulate cell-cell interactions in hES cells. To test whether the observed function of RRM signaling in cell-cell contacts in mES cells is conserved in hES cells, H1 cells grown under the feeder-free condition with Matrigel™ and conditioned medium (CM) (FIG. 3A) were treated with C3 exoenzyme. Cells treated with C3 showed clear cell-cell disintegration seen in mES cells, which suggests the conserved role of Rho signaling in human (FIG. 3B). Rock-inhibitor treatment also led to cell adhesion defects although it required a higher concentration (20 μM) than that (10 μM) for mES cells (FIG. 3C). Myosin IIA and IIB were colocalized with cell-cell borders in hES cells, which indicates their potential role in cell-cell adhesions (FIG. 3D). Supporting this, treatment with blebbistatin, a synthetic inhibitor highly selective for myosin II, led to remarkable cell-cell disintegration mirroring the phenotype of inhibition of Rho or Rock (FIG. 3D). These data indicate that both human and mouse ES cells utilize the RRM signaling axis as a core regulator of cell-cell interactions.

Figure 4:
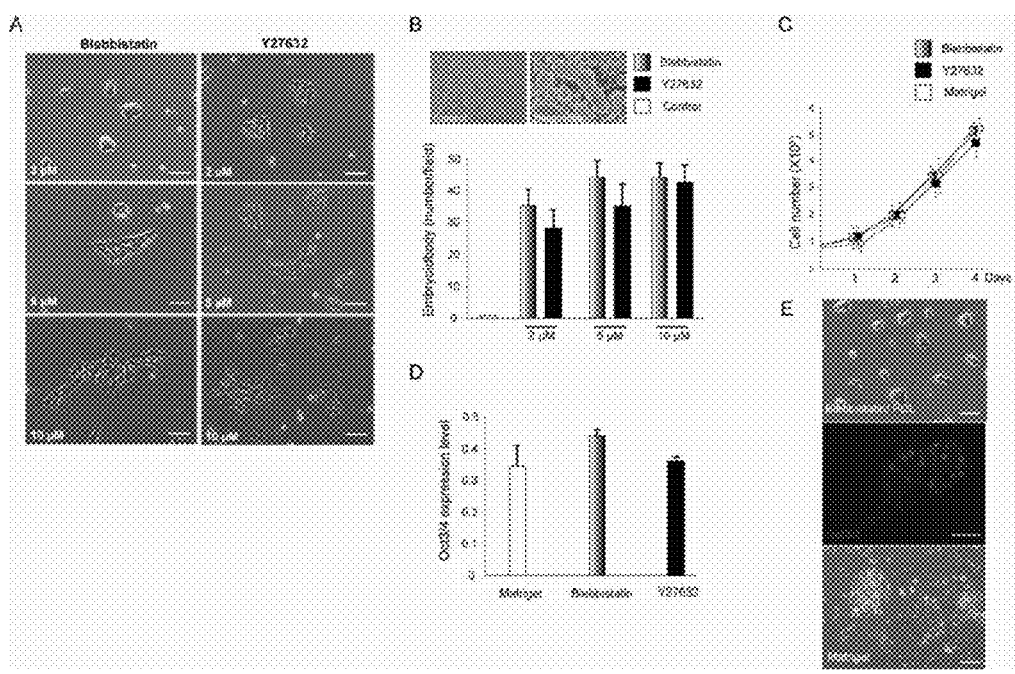
FIG. 4A-E shows a myosin II selective inhibitor, blebbistatin, enhances cell-matrix interactions, cell survival, and self-renewal of human induced pluripotent stem (iPS) cells under a defined condition. (A) Morphology of hiPS cells treated with blebbistatin or Y27632 at different concentrations on PDL coating. hiPS cells do not attach PDL coating in the absence of the inhibitors (data not shown). (B) Embryoid body formation of hiPS cells in suspension culture treated with different concentrations of blebbistatin or Y27632. The number of embryoid body in 5 different fields was counted under microscope. Data are mean±SD, n=5. Similar results were observed in three independent experiments. (C) Cell growth of hiPS cells grown on Matrigel or PDL in the presence of blebbistatin or Y27632 at 2.5 μM. (D) Expression of Oct3/4 in hiPS cells grown on Matrigel or PDL in the presence of blebbistatin or Y27632 at 2.5 μM as determined by QPCR. (E) Morphology of hiPS cells grown on PDL coating with blebbistatin at 2.5 μM for 15 passages (top). The middle panel shows Oct3/4 expression in hiPS cells grown under the same condition as assessed by immunocytochemistry. hiPS cells grown on Matrigel demonstrate the mixture of undifferentiated colonies and differentiated fibroblastic cells (bottom). Scale bars, 50 μm except for (E) bottom panel, 100 μm.

Myosin II controls cell-matrix contacts and detachment-induced apoptosis in hiPS and hiES cells. To test whether myosin II also acts as a major regulator of cell-matrix contacts downstream of Rock, hiPS cells were treated with blebbistain at different concentrations. hiPS and hES cells normally do not attach poly-D-lysine (PDL), a chemically synthesized matrix, when grown in mTeSR, a fully defined medium for human pluripotent stem cells. However, blebbistatin significantly supported attachment of hiPS cells on PDL at a minimum concentration of 2 μM, at which no signs of defects in cell-cell adhesions were observed (FIG. 4A). At higher concentrations, blebbistatin-treated hiPS cells exhibited disintegration of cell-cell contacts at a level comparable to that of Y27632-treated cells (FIG. 4A). Similar results were obtained from the experiments using hES cells. These data indicate that RRM signaling also controls cell-matrix interactions in human pluripotent stem cells.

While hiPS and hES cells can form cell aggregates and subsequently grow as embryoid bodies when plated at high densities on non-adhesive culture surfaces such as non-tissue culture-treated plates, they mostly undergo apoptosis when plated at low densities that prevent cells from forming aggregates. This is because human pluripotent stem cells are epithelical cells that are programmed to activate cell death signals upon detachment from culture surface (anoikis). A recent report demonstrated that inhibition of Rock in hES cells by Y27632 substantially increased cell survival at a clonal density on Matrigel and at a low density under suspension culture although underlying mechanisms remained unaddressed. Because the disclosure demonstrates that myosin II as a major effector downstream of Rock in cellular interactions, and myosin II has been directly implicated in apoptosis of non-adherent cells such as lymphocytes, it was hypothesized that myosin II also plays a role in regulating anoikis of iPS cells. Strikingly, hiPS cells and hES cells treated with blebbistatin markedly increased cell survival at a comparable level or more potent than that of Y27632 in low-density suspension culture (FIG. 4B). This indicates that inhibition of myosin II function is solely sufficient for replacing the anti-apoptotic effect mediated by Rock repression.

A combination of defined factors, blebbistatin and poly-D-lysine (PDL)-coating, efficiently supports self-renewal of human pluripotent stem cells. Since these data collectively indicated that a selective myosin II inhibitor, blebbistatin, dramatically enhances cell-matrix interactions and detachment-induced apoptosis of hES and iPS cells, further experiments were performed to evaluate whether hiPS cells can continuously self-renew under a fully defined culture condition based on a combination of blebbistatin, PDL-coating, and mTeSR. In this culture method, blebbistatin was used at 2.5 μM which is the minimum sufficient for supporting cell-matrix interactions but not affecting cell-cell adhesions of hiPS cells. Because blebbistatin-mediated complete inhibition of myosin II at high concentrations (50~100 μM) was known to affect cytokinesis as is the case with the complete inhibition of Rock by Y27632, it is important to avoid any adverse effects by using a minimally required concentration. Throughout over 15 passages under a defined condition using blebbistatin, hiPS cells were able to self-replicate at a constant growth rate comparable to that of cells treated with Y27632 without any signs of cytokinesis defects such as multinucleated cells (FIG. 4C). Maintenance of pluripotency markers, Oct3/4, Nanog, and Sox2, was confirmed by immunocytochemistry and QPCR (FIGS. 4D and 4E). Similar results were obtained from experiments using hES cell lines. Interestingly, although the hiPS cell line used in this study was prone to undergo differentiation when grown under the standard feeder-free condition using Matrigel™ (FIG. 4E, bottom panel), the vast majority of cells grown under the new method using blebbistatin maintained undifferentiated morphology of colonies with strong Oct3/4 expression, highlighting the superiority of the new method over the traditional feeder-free procedure (FIG. 4E, top and middle panels).

Inhibition of NMII by Blebbistatin Enhances Cloning Efficiency of hPS Cells.

Figure 6:
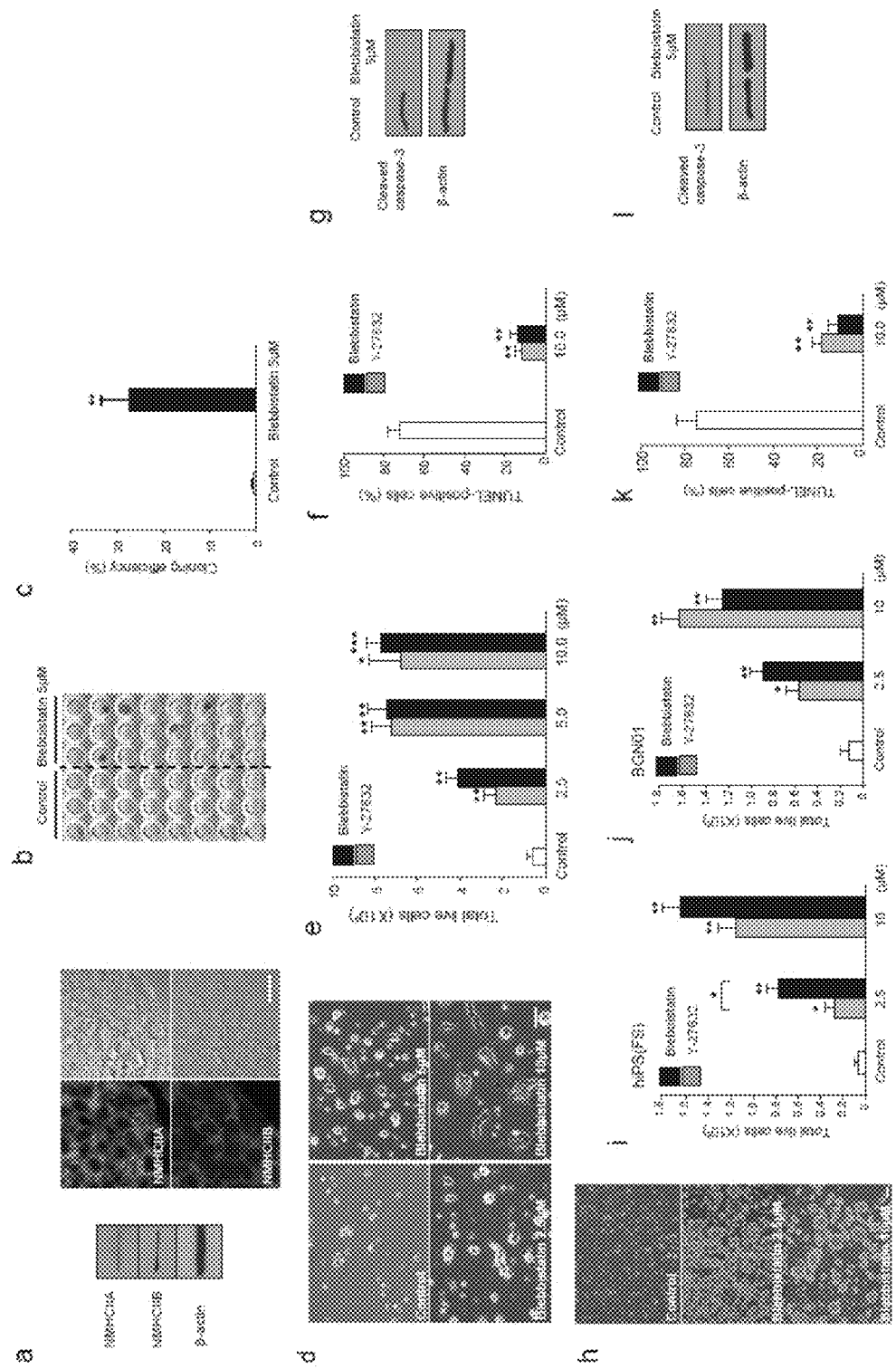
FIG. 6A-L shows inhibition of NMII by blebbistatin enhances survival of hPS cells under clonal and suspension culture conditions. (a) Expression of NMHCIIA and IIB in hES cells as determined by Western and immunocytochemical analyses. β-actin was used as a loading control. (b) Clonal assay of hiPS cells evaluated by ALP assay. hiPS cells were plated at a single cell per well in 96-well plates in the presence or absence of blebbistatin at 5 μM for 7 days, and subsequently evaluated by ALP assay. (c) Cloning efficiency was determined by the ratio of the number of wells with an ALP-positive colony to the number of wells seeded. Data are mean±SD, **p<0.01, n=3. Similar results were obtained from hES cells. (d-g) Cell viability assay of hiPS cells under adherence conditions. Cells were plated at $1 \times 10^5$ cells/well on PDL-coated 12-well plates in triplicates. After 24 h, cells were photographed (d), and the number of viable cells was counted by trypan blue exclusion assay (e). Cells plated with blebbistatin showed survival rates substantially higher than that of control. Data are mean±SD, *p<0.05, p<0.01, *p<0.001, n=3. The same experiment was repeated at least 3 times per cell line, and representative data are shown. Identical patterns of responses to blebbistatin or Y-27632 at different concentrations were repeatedly observed for each individual cell line. Similar results were obtained from hES cells. (f) Evaluation of apoptosis of hiPS cells. Cells used for cell viability assay in (e) were subjected to TUNEL assay. Data are mean±SD, *p<0.05, **p<0.01, n=3. (g) Cells plated under the same condition as shown in (e) were evaluated by Western analysis using an antibody against cleaved caspase-3. β-actin was used as a loading control. (h-l) Blebbistatin treatment increases survival of hPS cells in suspension culture. hiPS(FS) or hES (BGN01) cells were grown in suspension culture in the presence or absence of blebbistatin or Y-27632 for 2 days, subsequently photographed (hiPS cells are shown) (h), and subjected to live cell counting (i,j). TUNEL assay (k) and Western analysis detecting cleaved caspase-3 (l) were also carried out (data from hiPS cells are shown). Data are mean±SD, *p<0.05, **p<0.01, n=3. β-actin was used as a loading control. Scale bars, 25 μm.

The heavy chain of NMII (NMHCII) has three isoforms, of which NMHCIIA and NMHCIIB but not NMHCIIC are readily detectable in independent hES and iPS cell lines by Western analysis (FIG. 6a). Immunocytochemical analysis demonstrated that both isoforms were predominantly localized to plasma membranes in the undifferentiated hPS cells, consistent with their role in cell-cell contacts (FIG. 6a). In order to evaluate the function of NMII in cell death of hPS cells, blebbistatin was used, a synthetic chemical compound that effectively and reversibly blocks ATPase activity of NMII, thereby repressing motor function. The viability of hES and hiPS cells plated on Matrigel-coated plates at clonal density which is an initial critical hurdle to establish individual clonal lines was determined. Single hiPS cells were plated in each well of Matrigel-coated 96-well plates and undifferentiated colony formation was evaluated by alkaline phosphatase staining at 7 days after plating. While no or only a few colonies were formed under the control condition at 7 days after plating, approximately 30% of wells contained single colonies when cells were treated with blebbistatin ($0.47\pm0.25\%$ versus $29\pm1.8\%$, $p<0.01$) (FIG. 6b,c). Similar results were obtained from hES cells. This cloning efficiency was comparable to the reported efficiency by using Y-27632. Some of the colonies were selected, further expanded, and determined to be pluripotent through a series of molecular and functional analyses including detection of pluripotency markers and in vitro as well as in vivo differentiation assays.

Increased Survival of hPS Cells Under Adhesive Condition by Blebbistatin Treatment.

The cytoprotective effect of blebbistatin was detectable within a short period of time after plating. Cells ($1 \times 10^5$ cells/well, 12-well plates) were treated with or without blebbistatin at different concentrations, and the viability was evaluated by direct cell counting at 24 h after plating. hiPS cells treated with blebbistatin survived in significantly higher numbers than control (the highest effect was observed between 5 and 10 μM) on different substrates such as poly-D-lysine (PDL) ($7.9 \pm 0.6 \times 10^4$ cells at 10 μM versus $0.5 \pm 0.26 \times 10^4$ cells, n=3, p<0.001) and Matrigel coating ($8.6 \pm 0.6 \times 10^4$ cells at 10 μM versus $1.8 \pm 0.25 \times 10^4$ cells, n=3, p<0.01) (FIG. 6d,e, and FIG. 10a-d). Y-27632 was also tested under the same conditions side by side, and found that the survival effect of blebbistatin was comparable to that of Y-27632 ($7.2 \pm 1.1 \times 10^4$ cells at 10 μM on PDL, n=3, p<0.05) (FIG. 6d,e, and FIG. 10a-d). This result inversely correlated with the level of apoptosis detected by terminal deoxynucleotidyltransferase dUTP nick end labeling (TUNEL) assay. More than 70% of cells in the control condition were positive for TUNEL staining while cells treated with blebbistatin exhibited significantly lower numbers of TUNEL-positive cells ($73 \pm 2.5\%$ versus $11 \pm 3.8\%$, n=3, p<0.01) (FIG. 6f). This result was further confirmed by another indicator of apoptosis, cleaved caspase-3, which by Western analysis was decreased in blebbistatin treated cells, showing a robust level of reduction of apoptotic cells after blebbistatin treatment (FIG. 6g). Similar results were obtained from experiments using hES cells.

Blebbistatin Prevents Cell Death of hPS Cells Under Suspension Condition.

Figure 10:
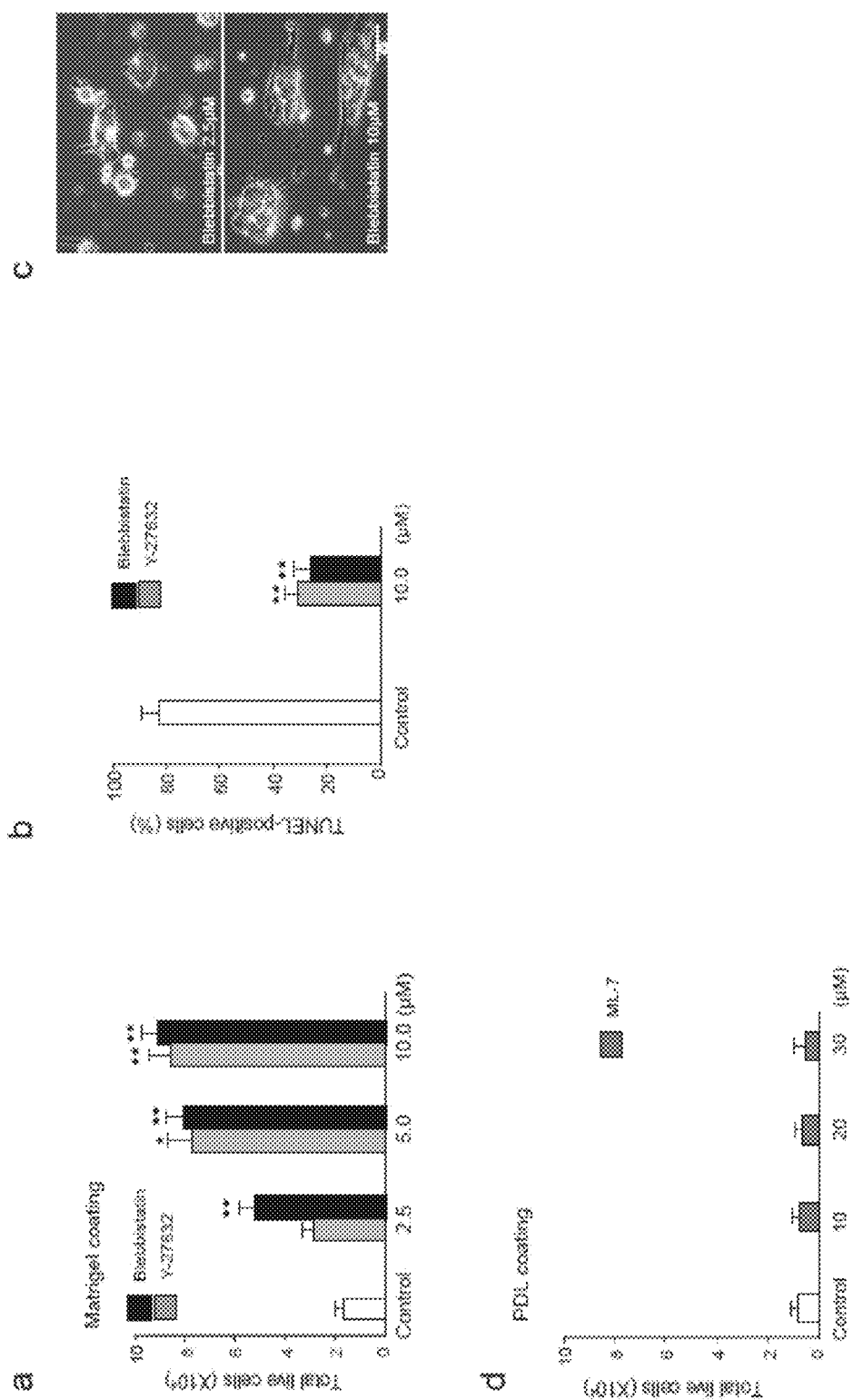
FIG. 10A-D shows blebbistatin treatment enhances survival of hPS cells under adherence condition. (a) hiPS cells were seeded at 1×10$^5$ cells/well on Matrigel-coated 12-well plates. After 24 h, the number of viable cells was counted by trypan blue exclusion assay. Data are mean±SD, *p<0.05, p<0.01, *p<0.001, n=3. (b) Apoptosis assay of hiPS cells. TUNEL-FITC-positive cells were determined under fluorescent microscope, and the ratio of the number of TUNEL-positive cells to the number of PI-positive cells was calculated. Data are mean±SD, *p<0.05, **p<0.01, n=3. (c) High power view of phase contrast images of hiPS cells grown on PDL-coated dishes in medium with blebbistatin at different concentrations for 24 h. Note the elongated cellular processes of adhered cells treated with blebbistatin. (d) An inhibitor of MLCK, ML-7, was tested for cell viability assay using hiPS cells plated on PDL-coated dishes at different concentrations. No significant increase in cell survival was observed. Similar results were obtained from experiments using hES cells. Scale bars, 25 μm.
Figure 11:
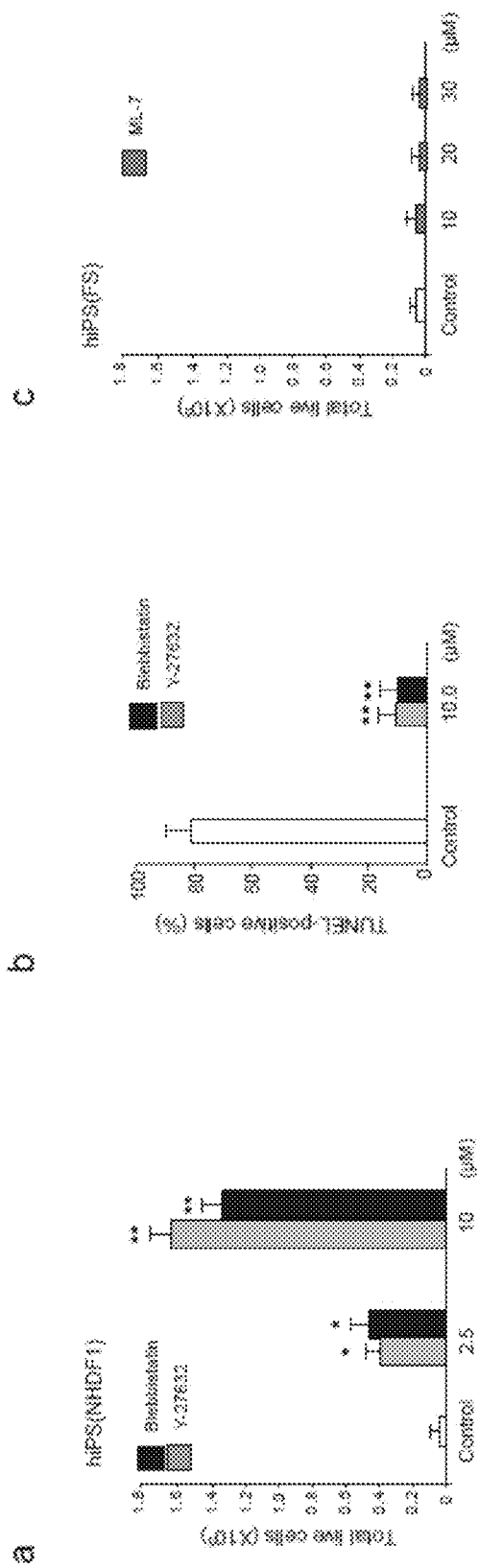
FIG. 11A-C shows increased survival of hiPS cells grown in suspension culture by blebbistatin. hiPS(NHDF1) cells were grown in suspension culture in the presence or absence of blebbistatin or Y-27632 for 2 days, and subjected to live cell counting (a) and TUNEL assay (b). Data are mean±SD, *p<0.05, **p<0.01, n=3. (c) hiPS cells grown under suspension condition were treated with ML-7 at various concentrations. No difference in the survival rate was observed in cells treated with ML-7.

In order to test whether blebbistatin is also effective on cells without cell-matrix adhesion, cells were grown in suspension culture which is a common primary step to generate embryoid bodies in standard differentiation protocols. Remarkably, blebbistatin treatment increased viability of hiPS cells to a level significantly higher than that of control under suspension conditions ($1.6 \pm 0.12 \times 10^5$ cells at 10 μM versus $0.05 \pm 0.02 \times 10^5$ cells, n=3, p<0.01) (FIG. 6h,i). hES cells and the other independent hiPS cell lines showed a comparable survival effect by blebbistatin (FIG. 6j and FIG. 11a). This result was supported by TUNEL and cleaved caspase-3 assays demonstrating significantly lower levels of apoptosis in the blebbistatin treatment condition (FIG. 6k,l, FIG. 11b). It is of note, however, that at a lower concentration, blebbistatin treatment consistently yielded higher viability than Y-27632, whereas at 10 μM, the survival effect of blebbistatin or Y-27632 was variable depending on individual cell lines (FIG. 6i,j and FIG. 11a). Thus blebbistatin provides an alternative strategy to protect hPS cells based on the dose and effectiveness on each cell line. Interestingly, ML-7, an inhibitor of myosin light chain kinase (MLCK) which is involved in the regulation of myosin-mediated contractility and apoptosis in other cell types did not show a significant effect on survival (FIGS. 10d, and 11c). This suggests that the function of NMII in the cell death regulation of pluripotent stem cells may be mainly controlled by ROCK through myosin light chain phosphatase rather than MLCK, although further study is necessary to determine such a possibility.

Enhanced Survival of mES Cells Lacking NMHCIIA.

Figure 7:
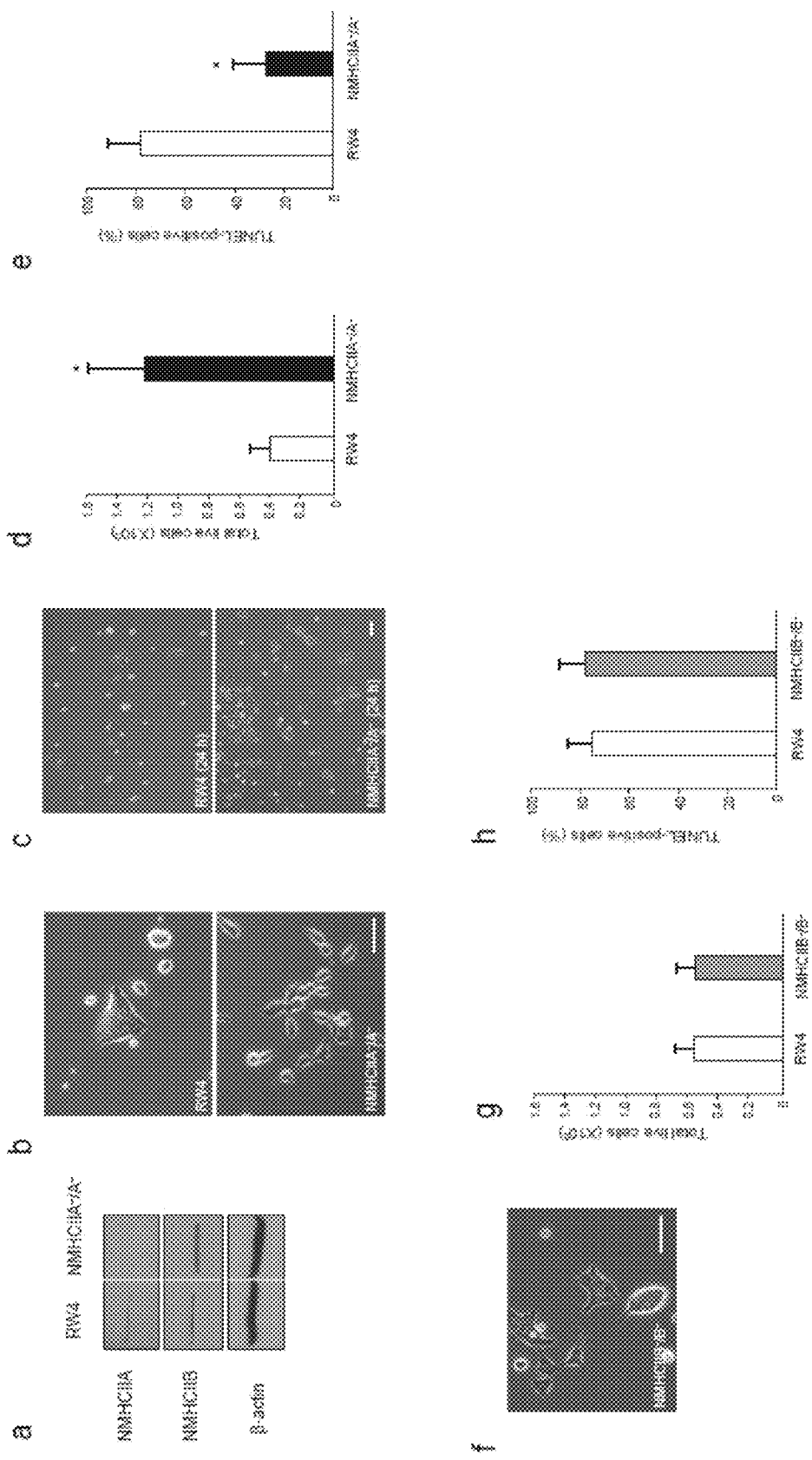
FIG. 7A-H show enhanced survival rate in NMHCIIA$^-$/A$^-$ mES cells. (a) Expression of NMHCIIA and NMHCIIB in parental wild type (RW4) and NMHCIIA$^-$/A$^-$ mutant mES cells was evaluated by Western analysis. β-actin was used as a loading control. (b) Morphology of RW4 and NMHCIIA$^-$/A$^-$ mutant cells grown on gelatin-coated plates. The mutant cells show loose cell-cell contact while RW4 cells exhibit tight cell-cell adhesions. (c-e) NMHCIIA$^-$/A$^-$ mES cells survive at a higher rate than that of RW4. Cells were plated at 1×10$^5$ cells/well on gelatin-coated 12-well plates in triplicates. After 24 h, cells were photographed (c), and evaluated by live cell counting (d) as well as TUNEL assay (e). The graphs are the representative data of three independent experiments. Data are mean±SD, *p<0.05, n=3. (f) Phase contrast image of NMHCIIB$^-$/B$^-$ mES cells. Cells maintain cell-cell adhesions. (c,d) NMHCIIB$^-$/B$^-$ mES cells were plated as described above and cell viability (g) and TUNEL (h) assays were carried out. Data are mean±SD, n=3. Scale bars, 25 μm.

To directly verify the role of NMII in cell viability at the genetic level, mutant mouse embryonic stem (mES) cells were used in which both alleles of the NMHCIIA gene are disrupted (NMHCIIA$^-$/A$^-$) (FIG. 7a). The cell-cell contacts of mutant cells were severely impaired (FIG. 7b). NMHCIIA$^-$/A$^-$ mES cells exhibited significantly higher viability than the parental line (RW4) at 24 h after plating ($1.3 \pm 0.3 \times 10^5$ cells versus $0.4 \pm 0.1 \times 10^5$ cells, n=3, p<0.05) (FIG. 7c,d), consistent with the data using blebbistatin for hPS cells. The level of apoptosis was also determined by TUNEL assay demonstrating considerably lower numbers of TUNEL-positive mutant cells as compared to the wild type mES cells (FIG. 7e).

It has been suggested that the two isoforms of NMII, NMIIA and NMIIB, have distinct functions in cell adhesion, migration, and contractility. To evaluated whether NMIIB also plays a role in the regulation of cell survival mutant mES cells genetically lacking NMHCIIB (NMHCIIB$^-$/B$^-$) (FIG. 7f) were examined. In contrast to the remarkable increase in the viability of NMHCIIA$^-$/A$^-$ mES cells, the NMHCIIB mutant showed a survival ratio similar to that of wild type mES cells ($0.54 \pm 0.1 \times 10^5$ cells versus $0.55 \pm 0.14 \times 10^5$ cells, n=3) (FIG. 7g,h). These results indicate that distinct regulatory mechanisms may control each isoform of NMII in the regulation of cell death of pluripotent stem cells as is the case with cell adhesion and migration.

Mechanistic Connection Between NMII and Self-Renewal Regulators.

Figure 8:
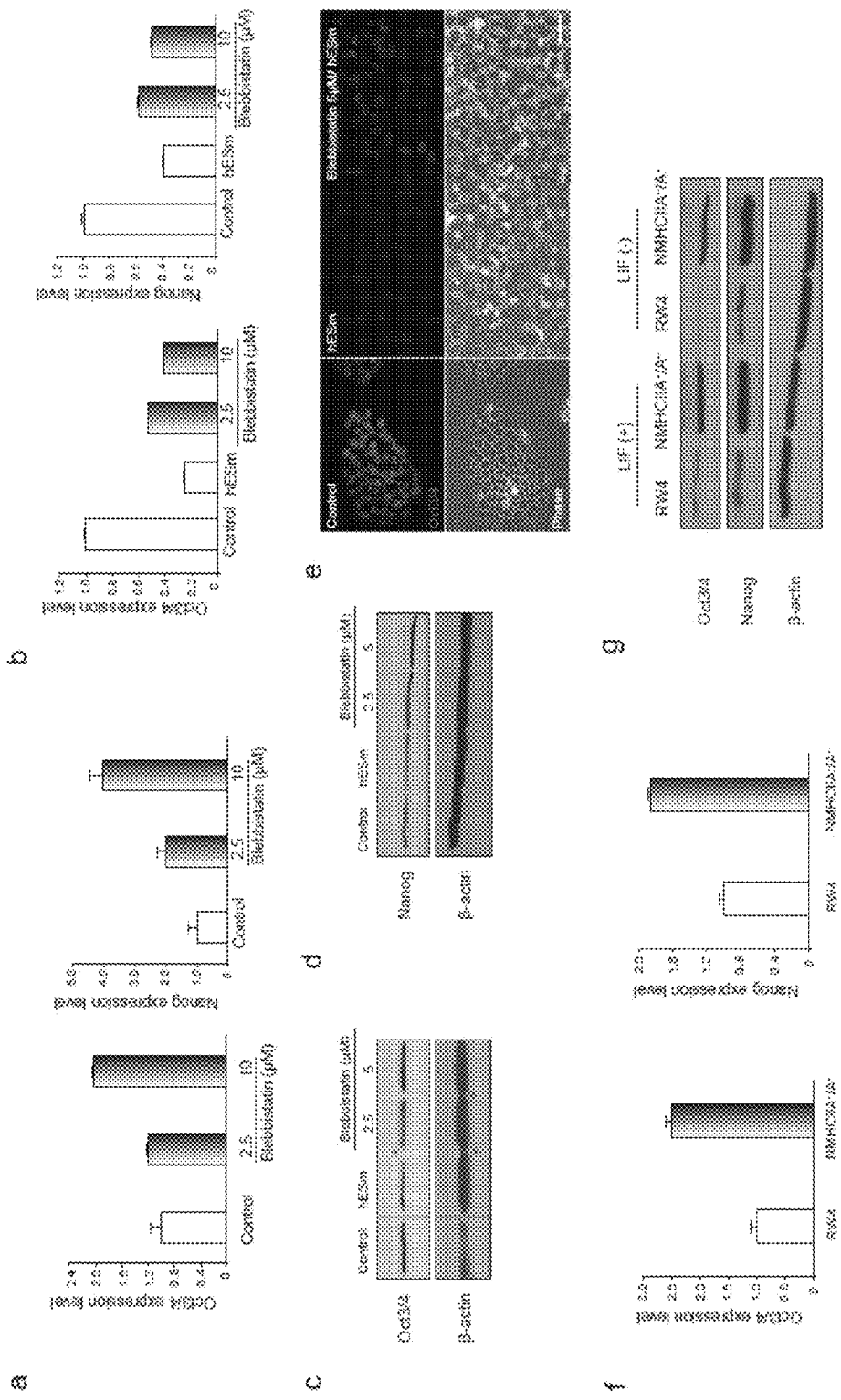
FIG. 8A-G show inhibition of NMII enhances expression of self-renewal regulators in human and mouse pluripotent stem cells. (a-d) hES cells were plated at 1×10$^5$ cells/well on Matrigel-coated 6-well plates in mTeSR without blebbistatin. After 24 h, medium was changed to fresh mTeSR or hESm with or without blebbistatin at different concentrations. At 48 h after switching medium, cells were harvested for RNA or protein extraction. Oct3/4 and Nanog expression was determined by QPCR from cells grown in mTeSR (a) or hESm (b), or by Western analysis from cells grown in hESm (c,d). The condition of cells grown in mTeSR without blebbistatin is indicated as 'control'. Similar results were obtained from hiPS cells (data not shown). For QPCR, the data were normalized to the expression level of β-actin. Expression levels on the Y-axis are shown in arbitrary units (control is set to 1.0). For Western analysis, β-actin was used as a loading control. (e) Cells grown under the same conditions (hESm with or without blebbistatin at 5 μM) were also subjected to immunocytochemistry to detect Oct3/4 expression. The images were captured with exactly the same parameters between each condition including exposure time for each filter. Phase contrast images showed that cells grown in hESm exhibited large and flat morphology while cells grown in mTeSR (control) maintained compact and tight morphology. Scale bar, 25 μm. (f) Expression of Oct3/4 and Nanog in the wild type (RW4) and NMHCIIA$^-$/A$^-$mES cells grown in the presence of leukemia inhibitory factor (LIF) was analyzed by QPCR. The data were normalized to the expression level of β-actin. Control is set to 1.0. (g) The same set of mES cell lines grown in the presence or absence of LIF for 2 d was evaluated by Western analysis. β-actin was used as a loading control.

In searching an array data base, NMHCIIA transcripts were recognized as being significantly enriched in the differentiated state of hES cells (Table 1), suggesting a potential molecular link between self-renewal/differentiation programs and NMII. Self-renewal regulators such as Oct3/4 and Nanog and NMII were examined and are mechanistically connected in hPS cells. hiPS or hES cells were grown in either mTeSR which supports the undifferentiated state or non-conditioned human ES medium (hESm) that induces passive differentiation in the presence or absence of blebbistatin at different concentrations for 48 h. hES cells treated with blebbistatin demonstrated elevated levels of both transcription factors in a dose dependent manner under both medium conditions as determined by quantitative RT-PCR (QPCR), Western analysis, and immunocytochemistry (FIG. 8a-e). Similar results were obtained from hiPS cells. To determine if this connection is also conserved in mouse, mES cells grown in the presence or absence of leukemia inhibitory factor (LIF) for 2 days were examined. Consistent with the data from hES cells, both of the self-renewal regulators, Oct3/4 and Nanog, were expressed at substantially higher protein levels in NMHCIIA$^-$/A$^-$ mES cells as compared to the parental cells under each condition (FIG. 8f,g). These data collectively suggest that NMII may function as a causal rather than a consequential factor in the negative regulation of self-renewal in both human and mouse pluripotent stem cells. This connection could be mediated by the interactions between NMII and β1 integrin at focal adhesions which, in turn, activate multiple pathways including ERK signaling that has been implicated in differentiation of ES cells. Alternatively, NMII may crosstalk with other self-renewal pathways such as TGF-β, PI3 kinase, and Wnt signaling. The upregulation of self-renewal regulators by inhibition of NMII may contribute to the enhanced survival of self-renewing pluripotent stem cells.

TABLE 1

Expression intensity of NMHCII isoforms in the undifferentiated or differentiated state of hES cells by Microarray analysis

| Probe ID | Gene Name | Undifferentiated | Differentiated |
| --- | --- | --- | --- |
| 211926_s_at | NMHC IIA | 326 | 2401.2 |
| 212372_at | NMHC IIB | 2177.4 | 2125.3 |
| 217660_at | NMHC IIC | 10.4 | 8 |

TABLE 2

Evaluation of the expression of class II myosins in the undifferentiated or differentiated state of hES cells by Microarray analysis

| Probe ID | Gene Name | Undifferentiated | Differentiated |
| --- | --- | --- | --- |
| 205951_at | MYH1 | 1.4 | 18 |
| 204631_at | MYH2 | 37.3 | −1.8 |
| 205940_at | MYH3 | 1.5 | 2.3 |
| 208148_at | MYH4 | 3.4 | 2.8 |
| 204737_s_at | MYH7 | 1.3 | 10.5 |
| 206717_at | MYH8 | 11.2 | 8.8 |
| 207961_x_at | MYH11 | 7.7 | 11 |

Establishment of Fully Defined Culture Condition for hPS Cells Using Blebbistatin.

Figure 9:
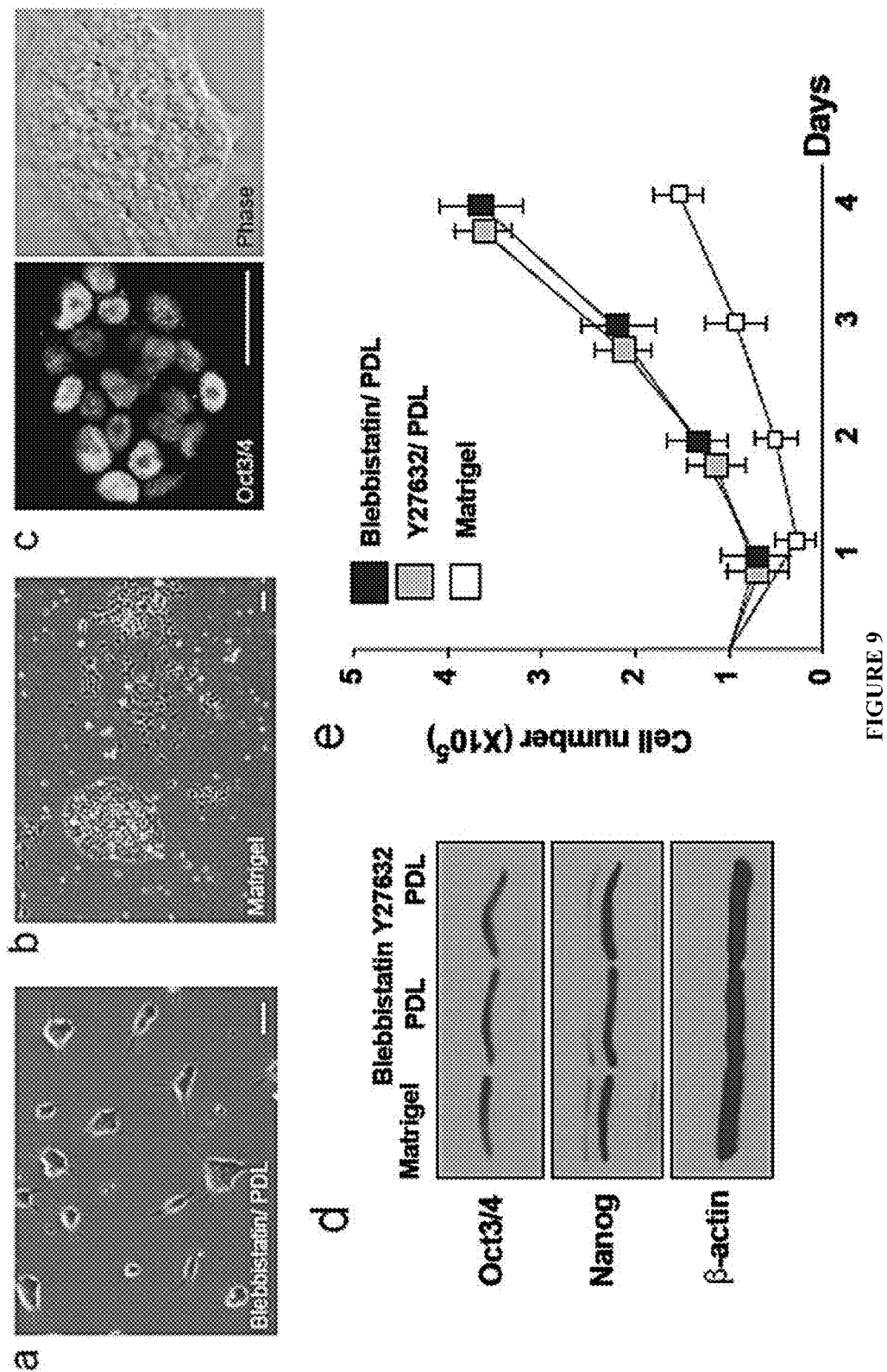
FIG. 9A-H show blebbistatin treatment supports self-renewal of hPS cells under a fully defined condition. (a-d) hiPS cells were grown on PDL in the presence of blebbistatin for 20 passages. Morphology of hiPS cells under blebbistatin/PDL condition (a) or standard feeder-free condition (Matrigel®) (b) is shown. High power view of Oct3/4 expression or phase contrast image of cells grown under blebbistatin/PDL conditions evaluated by immunofluorescence using confocal microscopy (c). (d) Oct3/4 and Nanog expression in cells grown under standard feeder-free (Matrigel), blebbistatin/PDL, or Y-27632/PDL condition was evaluated by Western analysis. β-actin was used as loading control. (e) Cell growth curve of hiPS cells cultured under blebbistatin/PDL, Y-27632/PDL, or standard feeder-free (Matrigel) conditions was determined by counting live cell number. Each data point shows mean±SD, n=3. The population doubling time of cells grown under blebbistatin/PDL, Y-27632/PDL, or standard feeder-free condition was approximately 32.1 h, 32.2, or 31.8 h, respectively. Similar results were obtained from hES cells. (f) Cells grown under blebbistatin/PDL condition for 20 passages were harvested, and approximately 2×10$^6$ cells were subcutaneously injected into SCID/beige mice. After 4 to 8 weeks, teratomas were collected, and subjected to histological assessment. The presence of 3 germ layer-derived tissues in each teratoma sample was confirmed. (g) The paraffin-embedded teratoma sections were examined by immunofluorescence analysis. Tissue specific markers such as nestin, α-fetoprotein, and α-smooth muscle actin were detected in teratoma-derived tissues. (h) hiPS(FS) cells grown under the defined condition (blebbistatin/PDL) for 20 passages were subjected to karyotyping by standard G-banding, and confirmed to maintain chromosomal integrity. Scale bars, 25 μm.
Figure 9:
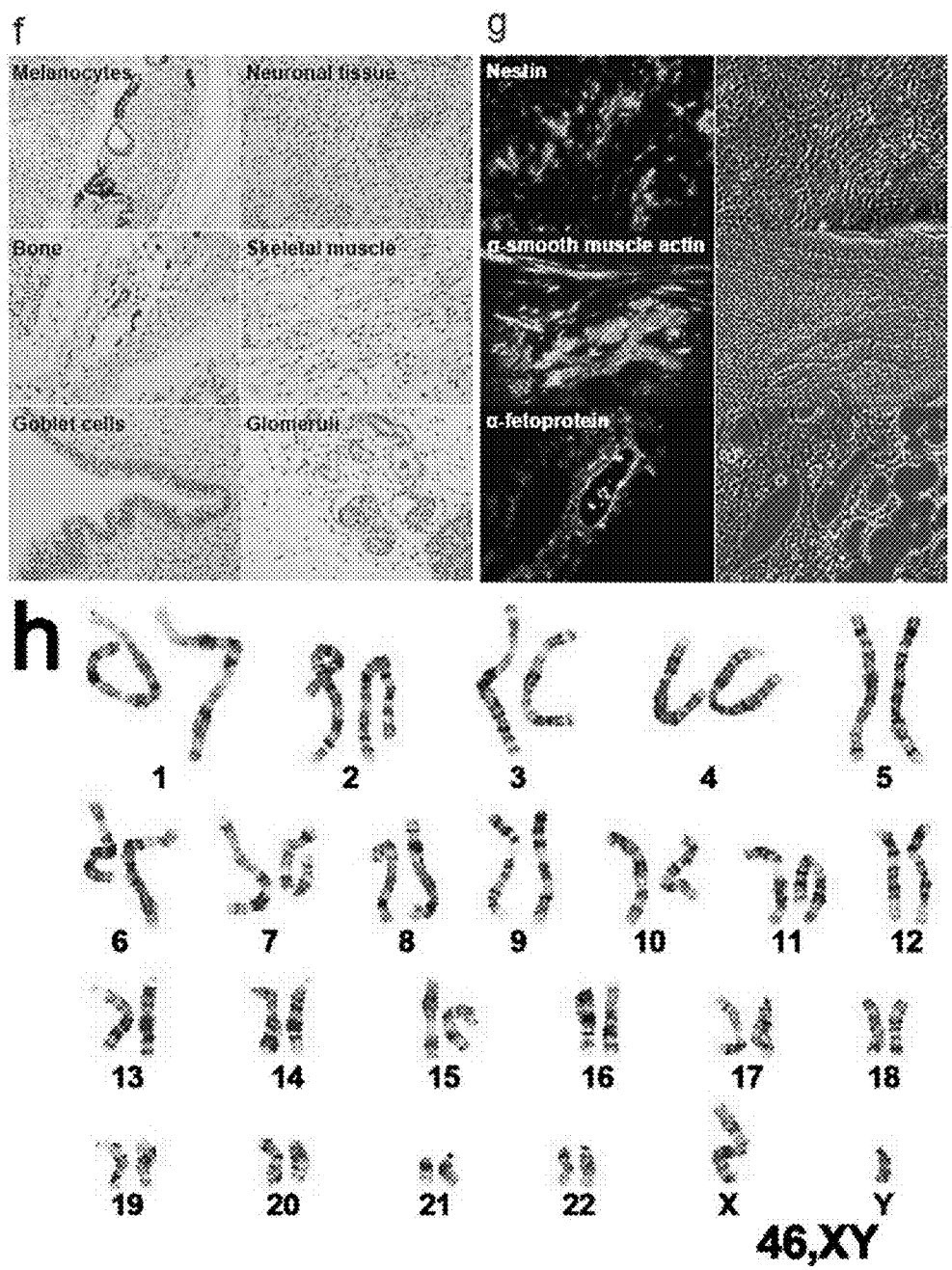
Figure 12:
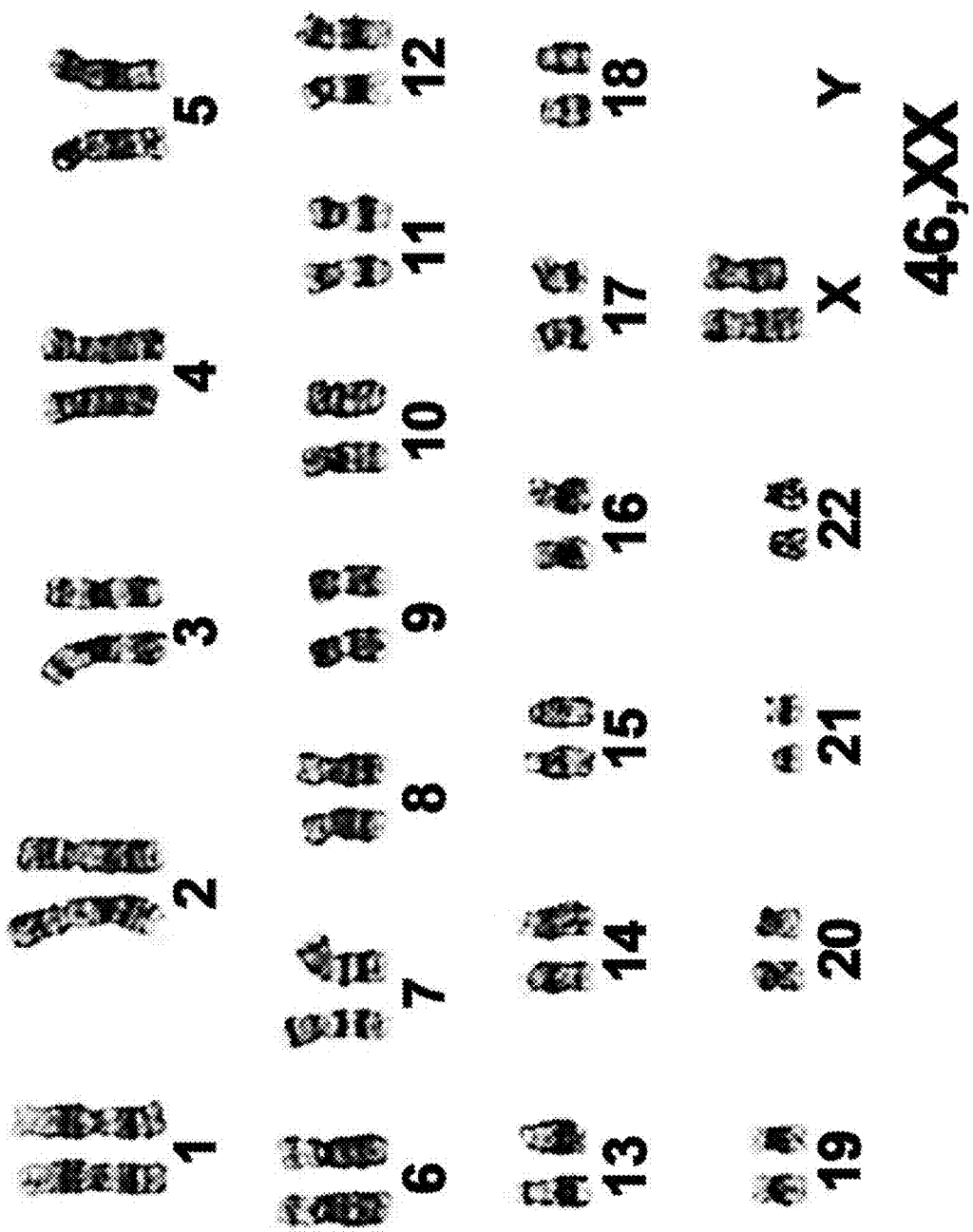
FIG. 12 shows maintenance of chromosomal integrity in hES cells cultured under the defined condition. hES (H9) cells were grown under the defined condition (blebbistatin/PDL) for 20 passages, and evaluated by standard G-banded karyotyping. A female karyotyping without abnormalities was confirmed.

The disclosure demonstrates that Y-27632 treatment enables hES cells to self-renew on PDL-coating, on which hES cells do not normally grow. Because PDL is a chemically synthesized substrate unlike Matrigel, a mouse tumor-derived extract, the disclosure provides a fully defined condition for self-renewal of hES cells using a defined medium. As blebbistatin accurately replicates all of the effects of Y-27632 on both hES and iPS cells, blebbistatin alone was tested to determine if it can fully replace Y-27632 in the defined culture condition. Blebbistatin was used at concentrations between 2.5 and 5 µM which are the minimum concentrations sufficient for supporting self-renewal but not affecting cell-cell adhesions. The required minimum concentration of blebbistatin varies depending on individual hES or hiPS cell lines although most of the lines self-renew at 5 µM of blebbistatin. As the strong inhibition of NMII by blebbistatin at high concentrations (50~100 µM) affects cytokinesis (also seen at high concentrations of Y-27632[8]), it is important to use blebbistatin at minimum concentrations. The maintenance of typical undifferentiated morphology and expression of pluripotency markers was confirmed in each line after 20 passages under this defined condition (FIG. 9a-d). hiPS or hES cells were able to self-renew on PDL at a constant growth rate comparable to that of cells treated with Y-27632 or cells grown under regular feeder-free conditions using Matrigel (FIG. 9e). In order to assess full differentiation functions in vivo, the passaged cells were subjected to teratoma assay by subcutaneously injecting them into severe combined immunodeficient (SCID)/beige mice. The teratoma samples were examined by histological sections, and determined to contain all three germ-layer derived differentiated tissues such as melanocytes (ectoderm), neuronal tissue (ectoderm), bone (mesoderm), skeletal muscle (mesoderm), gastrointestinal-like mucosal epithelium with goblet cells (endoderm), and glomeruli (endoderm) (FIG. 9f). This was further validated by immunohistochemistry detecting specialized cell-specific marker proteins (FIG. 9g). These results confirmed that hES or hiPS cells grown under the defined condition with blebbistatin can self-renew for an extended period of time without compromising multi-differentiation capacities, verifying the full reversibility of the effect of blebbistatin. The cells were determined to maintain genomic integrity as evaluated by karyotyping (hiPS cells in FIG. 9h, and hES cells in FIG. 12). The use of blebbistatin could be advantageous in pinpointing NMII function over that of Y-27632 which is likely to affect numerous effector molecules downstream of ROCK. In addition, blebbistatin is more cost-effective than Y-27632 for routine use. It has been suggested that fully reprogrammed hiPS cells can be generated in feeder-free conditions more efficiently than the traditional feeder-dependent culture conditions. Thus, this novel culture method may provide a basis to develop key technologies to efficiently derive and propagate new hiPS cell lines under fully defined conditions.

It should also be noted that hiPS cells treated with blebbistatin exhibited higher growth and cell survival rates than the cells treated with Y27632. Together with the fact that Rock has extended numbers of downstream effectors besides myosin II, the pinpoint inhibition of the principle regulator, myosin II, by blebbistatin have a great advantage over the use of Y27632 in precluding unnecessary outcomes by the inhibition of numerous downstream molecules other than myosin II.

Although a number of embodiments and features have been described above, it will be understood by those skilled in the art that modifications and variations of the described embodiments and features may be made without departing from the teachings of the disclosure or the scope of the disclosure as defined by the appended claims.

What is claimed is:

1. A composition comprising an animal product free, serum-free basal medium and a myosin II inhibitor.

2. The composition of claim 1, further comprising a ROCK inhibitor that binds to and inhibits a kinase domain of RHO.

3. The composition of claim 1, wherein the myosin II inhibitor is blebbistatin or analogue thereof.

4. The composition of claim 1, further comprising amino acids.

5. The composition of claim 4, wherein the amino acids are non-essential amino acids.

6. The composition of claim 1, further comprising a reducing agent.

7. The composition of claim 6, wherein the reducing agent is beta-mercaptoethanol.

8. The composition of claim 1, further comprising antibiotics and/or fungicides.

9. The composition of claim 1, further comprising a pyruvate salt.

10. The composition of claim 9, wherein the pyruvate salt is sodium pyruvate or potassium pyruvate.

11. The composition of claim 1, further comprising leukemia inhibitor factor (LIF).

12. The composition of claim 1, further comprising L-glutamine.

13. A stem cell culture, comprising stem cells in a composition of claim 1.

14. The stem cell culture of claim 13, wherein the myosin II inhibitor is blebbistatin or an analogue thereof.

15. A kit comprising a composition of claim 13.

16. A composition comprising an animal product free, serum-free basal medium supplemented with non-essential amino acids, an anti-oxidant, a reducing agent, growth factors, a pyruvate salt and a myosin II inhibitor.

17. The composition of claim 16, wherein the basal medium is DMEM.

18. A kit comprising poly-D-lysine, and a composition comprising a defined culture medium comprising an animal product free, serum-free basal medium and a myosin II inhibitor.

19. The kit of claim 18, further comprising a tissue culture substrate.

20. The kit of claim 18, further comprising a supplement comprising growth factors.

21. The kit of claim 18, wherein the defined culture medium further comprises recombinant bFGF, recombinant TGFI3, an osmolarity of about 330-350 mOsm, and a pH of 7.25 to 7.45.

22. The kit of claim 18, wherein the myosin II inhibitor is blebbistatin or an analogue thereof.

23. A method of culturing stem cells, comprising:
suspending the stem cells in a culture medium comprising a defined culture medium comprising an animal product free, serum-free basal medium and a myosin II inhibitor; and culturing the stem cells in the presence of a poly-D-lysine coated tissue culture substrate.

24. The method of claim 23, the defined culture medium further comprising recombinant bFGF, recombinant TGFI3, an osmolarity of about 330-350 mOsm, and a pH of 7.25 to 7.45.

* * * * *

SEQUENCE LISTING

```
<160> NUMBER OF SEQ ID NOS: 90

<210> SEQ ID NO 1
<211> LENGTH: 19
<212> TYPE: RNA
<213> ORGANISM: Artificial Sequence
<220> FEATURE:
<223> OTHER INFORMATION: ROCK I siRNA

<400> SEQUENCE: 1
gcaaagagau uguuagaau                                                   19

<210> SEQ ID NO 2
<211> LENGTH: 19
<212> TYPE: RNA
<213> ORGANISM: Artificial Sequence
<220> FEATURE:
<223> OTHER INFORMATION: ROCK I siRNA

<400> SEQUENCE: 2
agacacagcu guaagauua                                                   19
```

```
<210> SEQ ID NO 3
<211> LENGTH: 19
<212> TYPE: RNA
<213> ORGANISM: Artificial Sequence
<220> FEATURE:
<223> OTHER INFORMATION: ROCK I siRNA

<400> SEQUENCE: 3
ugucgaagau gccauguua                                                19

<210> SEQ ID NO 4
<211> LENGTH: 19
<212> TYPE: RNA
<213> ORGANISM: Artificial Sequence
<220> FEATURE:
<223> OTHER INFORMATION: ROCK I siRNA

<400> SEQUENCE: 4
gaccuucaag cacgaauua                                                19

<210> SEQ ID NO 5
<211> LENGTH: 21
<212> TYPE: RNA
<213> ORGANISM: Artificial Sequence
<220> FEATURE:
<223> OTHER INFORMATION: ROCK II siRNA

<400> SEQUENCE: 5
gagauuaccu uacggaaaau u                                             21

<210> SEQ ID NO 6
<211> LENGTH: 21
<212> TYPE: RNA
<213> ORGANISM: Artificial Sequence
<220> FEATURE:
<223> OTHER INFORMATION: ROCK II siRNA

<400> SEQUENCE: 6
uuuuccguaa gguaaucucu u                                             21

<210> SEQ ID NO 7
<211> LENGTH: 21
<212> TYPE: RNA
<213> ORGANISM: Artificial Sequence
<220> FEATURE:
<223> OTHER INFORMATION: ROCK II siRNA

<400> SEQUENCE: 7
ggacaugagu uuauuccuau u                                             21

<210> SEQ ID NO 8
<211> LENGTH: 21
<212> TYPE: RNA
<213> ORGANISM: Artificial Sequence
<220> FEATURE:
<223> OTHER INFORMATION: ROCK II siRNA

<400> SEQUENCE: 8
uaggaauaaa cucauguccu u                                             21

<210> SEQ ID NO 9
<211> LENGTH: 21
<212> TYPE: RNA
<213> ORGANISM: Artificial Sequence
<220> FEATURE:
<223> OTHER INFORMATION: ROCK II siRNA
```

-continued

```
<400> SEQUENCE: 9
gcaaugaagc uucuuaguau u                                          21

<210> SEQ ID NO 10
<211> LENGTH: 21
<212> TYPE: RNA
<213> ORGANISM: Artificial Sequence
<220> FEATURE:
<223> OTHER INFORMATION: ROCK II siRNA

<400> SEQUENCE: 10
uacuaagaag cuucauugcu u                                          21

<210> SEQ ID NO 11
<211> LENGTH: 21
<212> TYPE: RNA
<213> ORGANISM: Artificial Sequence
<220> FEATURE:
<223> OTHER INFORMATION: ROCK II siRNA

<400> SEQUENCE: 11
cacaacagau gaucaaauau u                                          21

<210> SEQ ID NO 12
<211> LENGTH: 21
<212> TYPE: RNA
<213> ORGANISM: Artificial Sequence
<220> FEATURE:
<223> OTHER INFORMATION: ROCK II siRNA

<400> SEQUENCE: 12
uauuugauca ucuguugugu u                                          21

<210> SEQ ID NO 13
<211> LENGTH: 19
<212> TYPE: RNA
<213> ORGANISM: Artificial Sequence
<220> FEATURE:
<223> OTHER INFORMATION: DIA 1 siRNA

<400> SEQUENCE: 13
guacagcugu gcguguuug                                             19

<210> SEQ ID NO 14
<211> LENGTH: 19
<212> TYPE: RNA
<213> ORGANISM: Artificial Sequence
<220> FEATURE:
<223> OTHER INFORMATION: DIA 1 siRNA

<400> SEQUENCE: 14
gaaguugucu guagaggaa                                             19

<210> SEQ ID NO 15
<211> LENGTH: 19
<212> TYPE: RNA
<213> ORGANISM: Artificial Sequence
<220> FEATURE:
<223> OTHER INFORMATION: DIA 1 siRNA

<400> SEQUENCE: 15
ggaacaguau aacaaacua                                             19

<210> SEQ ID NO 16
<211> LENGTH: 19
```

```
<212> TYPE: RNA
<213> ORGANISM: Artificial Sequence
<220> FEATURE:
<223> OTHER INFORMATION: DIA 1 siRNA

<400> SEQUENCE: 16
gaaaccagca ugagauuau                                            19

<210> SEQ ID NO 17
<211> LENGTH: 21
<212> TYPE: RNA
<213> ORGANISM: Artificial Sequence
<220> FEATURE:
<223> OTHER INFORMATION: DIA 2 siRNA

<400> SEQUENCE: 17
gaugaccgau cuugauuuu u                                          21

<210> SEQ ID NO 18
<211> LENGTH: 21
<212> TYPE: RNA
<213> ORGANISM: Artificial Sequence
<220> FEATURE:
<223> OTHER INFORMATION: DIA 2 siRNA

<400> SEQUENCE: 18
aaaucaaaga ucggucaucu u                                         21

<210> SEQ ID NO 19
<211> LENGTH: 21
<212> TYPE: RNA
<213> ORGANISM: Artificial Sequence
<220> FEATURE:
<223> OTHER INFORMATION: Mysoin IIA siRNA

<400> SEQUENCE: 19
gagcgagccu ccaggaauau u                                         21

<210> SEQ ID NO 20
<211> LENGTH: 21
<212> TYPE: RNA
<213> ORGANISM: Artificial Sequence
<220> FEATURE:
<223> OTHER INFORMATION: Mysoin IIA siRNA

<400> SEQUENCE: 20
uauuccugga ggcucgcucu u                                         21

<210> SEQ ID NO 21
<211> LENGTH: 21
<212> TYPE: RNA
<213> ORGANISM: Artificial Sequence
<220> FEATURE:
<223> OTHER INFORMATION: Myosin IIA siRNA

<400> SEQUENCE: 21
gcaccaagcu caagcagauu u                                         21

<210> SEQ ID NO 22
<211> LENGTH: 21
<212> TYPE: RNA
<213> ORGANISM: Artificial Sequence
<220> FEATURE:
<223> OTHER INFORMATION: Myosin IIA siRNA

<400> SEQUENCE: 22
aucugcuuga gcuuggugcu u                                         21
```

<210> SEQ ID NO 23
<211> LENGTH: 21
<212> TYPE: RNA
<213> ORGANISM: Artificial Sequence
<220> FEATURE:
<223> OTHER INFORMATION: Myosin IIA siRNA

<400> SEQUENCE: 23
gaaccgaacu ggccgacaau u          21

<210> SEQ ID NO 24
<211> LENGTH: 21
<212> TYPE: RNA
<213> ORGANISM: Artificial Sequence
<220> FEATURE:
<223> OTHER INFORMATION: Myosin IIA siRNA

<400> SEQUENCE: 24
uugucggcca guucgguucu u          21

<210> SEQ ID NO 25
<211> LENGTH: 21
<212> TYPE: RNA
<213> ORGANISM: Artificial Sequence
<220> FEATURE:
<223> OTHER INFORMATION: Myosin IIA siRNA

<400> SEQUENCE: 25
gaagguggcu gccuacgauu u          21

<210> SEQ ID NO 26
<211> LENGTH: 21
<212> TYPE: RNA
<213> ORGANISM: Artificial Sequence
<220> FEATURE:
<223> OTHER INFORMATION: Myosin IIA siRNA

<400> SEQUENCE: 26
aucguaggca gccaccuucu u          21

<210> SEQ ID NO 27
<211> LENGTH: 21
<212> TYPE: RNA
<213> ORGANISM: Artificial Sequence
<220> FEATURE:
<223> OTHER INFORMATION: Myosin IIB siRNA

<400> SEQUENCE: 27
ggacuuaucu auacuuacuu u          21

<210> SEQ ID NO 28
<211> LENGTH: 21
<212> TYPE: RNA
<213> ORGANISM: Artificial Sequence
<220> FEATURE:
<223> OTHER INFORMATION: Myosin IIB siRNA

<400> SEQUENCE: 28
aguaaguaua gauaaguccu u          21

<210> SEQ ID NO 29
<211> LENGTH: 21
<212> TYPE: RNA
<213> ORGANISM: Artificial Sequence
<220> FEATURE:
<223> OTHER INFORMATION: Myosin IIB siRNA

```
<400> SEQUENCE: 29
gagcguacau uucauaucuu u                                              21

<210> SEQ ID NO 30
<211> LENGTH: 21
<212> TYPE: RNA
<213> ORGANISM: Artificial Sequence
<220> FEATURE:
<223> OTHER INFORMATION: Myosin IIB siRNA

<400> SEQUENCE: 30
agauaugaaa uguacgcucu u                                              21

<210> SEQ ID NO 31
<211> LENGTH: 21
<212> TYPE: RNA
<213> ORGANISM: Artificial Sequence
<220> FEATURE:
<223> OTHER INFORMATION: Myosin IIB siRNA

<400> SEQUENCE: 31
ugaggcagcu aguauuaaau u                                              21

<210> SEQ ID NO 32
<211> LENGTH: 21
<212> TYPE: RNA
<213> ORGANISM: Artificial Sequence
<220> FEATURE:
<223> OTHER INFORMATION: Myosin IIB siRNA

<400> SEQUENCE: 32
uuuaauacua gcugccucau u                                              21

<210> SEQ ID NO 33
<211> LENGTH: 21
<212> TYPE: RNA
<213> ORGANISM: Artificial Sequence
<220> FEATURE:
<223> OTHER INFORMATION: Myosin IIB siRNA

<400> SEQUENCE: 33
guauuaaguu ugcgaaggau u                                              21

<210> SEQ ID NO 34
<211> LENGTH: 21
<212> TYPE: RNA
<213> ORGANISM: Artificial Sequence
<220> FEATURE:
<223> OTHER INFORMATION: Myosin IIB siRNA

<400> SEQUENCE: 34
uccuucgcaa acuuaauacu u                                              21

<210> SEQ ID NO 35
<211> LENGTH: 21
<212> TYPE: RNA
<213> ORGANISM: Artificial Sequence
<220> FEATURE:
<223> OTHER INFORMATION: Myosin IIC siRNA

<400> SEQUENCE: 35
cugaagaaag accgcaauau u                                              21

<210> SEQ ID NO 36
<211> LENGTH: 21
```

```
<212> TYPE: RNA
<213> ORGANISM: Artificial Sequence
<220> FEATURE:
<223> OTHER INFORMATION: Myosin IIC siRNA

<400> SEQUENCE: 36
uauugcgcuc uuucuucagu u                                              21

<210> SEQ ID NO 37
<211> LENGTH: 21
<212> TYPE: RNA
<213> ORGANISM: Artificial Sequence
<220> FEATURE:
<223> OTHER INFORMATION: Myosin IIC siRNA

<400> SEQUENCE: 37
ucaaggacca uuaccgaaau u                                              21

<210> SEQ ID NO 38
<211> LENGTH: 21
<212> TYPE: RNA
<213> ORGANISM: Artificial Sequence
<220> FEATURE:
<223> OTHER INFORMATION: Myosin IIC siRNA

<400> SEQUENCE: 38
uuucgguaau gguccuugau u                                              21

<210> SEQ ID NO 39
<211> LENGTH: 21
<212> TYPE: RNA
<213> ORGANISM: Artificial Sequence
<220> FEATURE:
<223> OTHER INFORMATION: Myosin IIC siRNA

<400> SEQUENCE: 39
acgcagaggu agagcgcgau u                                              21

<210> SEQ ID NO 40
<211> LENGTH: 21
<212> TYPE: RNA
<213> ORGANISM: Artificial Sequence
<220> FEATURE:
<223> OTHER INFORMATION: Myosin IIC siRNA

<400> SEQUENCE: 40
ucgcgcucua ccucugcguu u                                              21

<210> SEQ ID NO 41
<211> LENGTH: 21
<212> TYPE: RNA
<213> ORGANISM: Artificial Sequence
<220> FEATURE:
<223> OTHER INFORMATION: Myosin IIC siRNA

<400> SEQUENCE: 41
aggcggaacu ugagagcguu u                                              21

<210> SEQ ID NO 42
<211> LENGTH: 21
<212> TYPE: RNA
<213> ORGANISM: Artificial Sequence
<220> FEATURE:
<223> OTHER INFORMATION: Myosin IIC siRNA

<400> SEQUENCE: 42
acgcucucaa guuccgccuu u                                              21
```

<210> SEQ ID NO 43
<211> LENGTH: 21
<212> TYPE: RNA
<213> ORGANISM: Artificial Sequence
<220> FEATURE:
<223> OTHER INFORMATION: MYPT1 siRNA

<400> SEQUENCE: 43
gaacgagacu ugcguauguu u                                              21

<210> SEQ ID NO 44
<211> LENGTH: 21
<212> TYPE: RNA
<213> ORGANISM: Artificial Sequence
<220> FEATURE:
<223> OTHER INFORMATION: MYPT1 siRNA

<400> SEQUENCE: 44
acauacgcaa gucucguucu u                                              21

<210> SEQ ID NO 45
<211> LENGTH: 21
<212> TYPE: RNA
<213> ORGANISM: Artificial Sequence
<220> FEATURE:
<223> OTHER INFORMATION: MYPT1 siRNA

<400> SEQUENCE: 45
aagaauaguu cgaucaaugu u                                              21

<210> SEQ ID NO 46
<211> LENGTH: 21
<212> TYPE: RNA
<213> ORGANISM: Artificial Sequence
<220> FEATURE:
<223> OTHER INFORMATION: MYPT1 siRNA

<400> SEQUENCE: 46
cauugaucga acuauucuuu u                                              21

<210> SEQ ID NO 47
<211> LENGTH: 21
<212> TYPE: RNA
<213> ORGANISM: Artificial Sequence
<220> FEATURE:
<223> OTHER INFORMATION: MYPT1 siRNA

<400> SEQUENCE: 47
cgacaucaau uacgccaauu u                                              21

<210> SEQ ID NO 48
<211> LENGTH: 21
<212> TYPE: RNA
<213> ORGANISM: Artificial Sequence
<220> FEATURE:
<223> OTHER INFORMATION: MYPT1 siRNA

<400> SEQUENCE: 48
auuggcguaa uugaugucgu u                                              21

<210> SEQ ID NO 49
<211> LENGTH: 21
<212> TYPE: RNA
<213> ORGANISM: Artificial Sequence
<220> FEATURE:
<223> OTHER INFORMATION: MYPT1 siRNA

<400> SEQUENCE: 49
ucggcaaggu guugauauau u                                              21

<210> SEQ ID NO 50
<211> LENGTH: 21
<212> TYPE: RNA
<213> ORGANISM: Artificial Sequence
<220> FEATURE:
<223> OTHER INFORMATION: MYPT1 siRNA

<400> SEQUENCE: 50
uauaucaaca ccuugccgau u                                              21

<210> SEQ ID NO 51
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 51
cgaggcccag agcaagag                                                  18

<210> SEQ ID NO 52
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 52
cgtcccagtt ggtaacaatg c                                              21

<210> SEQ ID NO 53
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 53
attcattcct accctctacc actttc                                         26

<210> SEQ ID NO 54
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 54
gcttaaagac atgccacaaa ggt                                            23

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 55
gcgatgctga gcctgatgat                                                20

<210> SEQ ID NO 56
<211> LENGTH: 20

```
<212> TYPE: DNA
<213> ORGANISM: Artificial Sequence
<220> FEATURE:
<223> OTHER INFORMATION: Oligonucleotide primer

<400> SEQUENCE: 56
gcacaggcaa tgacaaccat                                                   20

<210> SEQ ID NO 57
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 57
ggatgcacag gaacagtata acaaa                                             25

<210> SEQ ID NO 58
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 58
aagacgaagt agtcacctag ctcctt                                            26

<210> SEQ ID NO 59
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 59
cagtcaggtg cagcattcag a                                                 21

<210> SEQ ID NO 60
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 60
gggtcttacc tggatttctt gga                                               23

<210> SEQ ID NO 61
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 61
tggcaagcaa gcgtgtgt                                                     18

<210> SEQ ID NO 62
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 62
gccgatgcgg tacaggtt                                                     18
```

```
<210> SEQ ID NO 63
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 63
tcctcacgcc caggatca                                              18

<210> SEQ ID NO 64
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 64
gccaatgctt ccactgcaa                                             19

<210> SEQ ID NO 65
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 65
gcaatgccaa gacggtgaa                                             19

<210> SEQ ID NO 66
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 66
gatgtagcca gcaatatcaa agttga                                     26

<210> SEQ ID NO 67
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 67
gactcccccg ggttcct                                               17

<210> SEQ ID NO 68
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 68
cctcagccca caaacgattt                                            20

<210> SEQ ID NO 69
<211> LENGTH: 18
<212> TYPE: DNA
<213> ORGANISM: Artificial Sequence
<220> FEATURE:
<223> OTHER INFORMATION: Oligonucleotide primer
```

<400> SEQUENCE: 69
tggcgtggag actttgca                                                    18

<210> SEQ ID NO 70
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 70
gaggttccct ctgagttgct ttc                                              23

<210> SEQ ID NO 71
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 71
tgtgcactca aggacaggtt tc                                               22

<210> SEQ ID NO 72
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 72
caggttcaga atggaggaga gttc                                             24

<210> SEQ ID NO 73
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 73
caacacgtct ccacccactt c                                                21

<210> SEQ ID NO 74
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 74
tttctggaac agtgacggtg aa                                               22

<210> SEQ ID NO 75
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 75
ccactgcaac cgtgctttt                                                   19

<210> SEQ ID NO 76
<211> LENGTH: 19

```
<212> TYPE: DNA
<213> ORGANISM: Artificial Sequence
<220> FEATURE:
<223> OTHER INFORMATION: Oligonucleotide Primer

<400> SEQUENCE: 76
cacatccgag tgggtttgg                                                    19

<210> SEQ ID NO 77
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 77
gggtctgttc cagagggatc a                                                 21

<210> SEQ ID NO 78
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 78
ggatcatccg catcaatgg                                                    19

<210> SEQ ID NO 79
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 79
gaagcctttc ccctgtctc t                                                  21

<210> SEQ ID NO 80
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 80
aagggcaggc acctcagtt                                                    19

<210> SEQ ID NO 81
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 81
aatgaaatct aagaggtggc agaaa                                             25

<210> SEQ ID NO 82
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 82
ttctgcgtca caccattgct                                                   20
```

<210> SEQ ID NO 83
<211> LENGTH: 16
<212> TYPE: DNA
<213> ORGANISM: Artificial Sequence
<220> FEATURE:
<223> OTHER INFORMATION: Oligonucleotide primer

<400> SEQUENCE: 83
gcagcccccg ggttaa                                                         16

<210> SEQ ID NO 84
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 84
gctccgactg cttgaatctt g                                                   21

<210> SEQ ID NO 85
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 85
ccattccacg cccagcta                                                       18

<210> SEQ ID NO 86
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 86
tcactcgccc caaagatgag                                                     20

<210> SEQ ID NO 87
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 87
ggattgtcct gtgccaactg t                                                   21

<210> SEQ ID NO 88
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 88
ggttcaccct cggcgttt                                                       18

<210> SEQ ID NO 89
<211> LENGTH: 18
<212> TYPE: DNA
<213> ORGANISM: Artificial Sequence
<220> FEATURE:
<223> OTHER INFORMATION: Oligonucleotide Primer

```
<400> SEQUENCE: 89
tggcgtggag actttgca                                                18

<210> SEQ ID NO 90
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 90
gaggttccct ctgagttgct ttc                                          23
```